US009750868B2

(12) United States Patent
Tobescu

(10) Patent No.: US 9,750,868 B2
(45) Date of Patent: Sep. 5, 2017

(54) MONITORING PRODUCT INTEGRITY OF A PHARMACEUTICAL PRODUCT IN A SYRINGE USING A MINIATURIZED ELECTRONIC SENSOR TAG

(71) Applicant: Q-TAG AG, Ganterschwil (CH)

(72) Inventor: Corneliu Tobescu, Wilen (CH)

(73) Assignee: Q-TAG AG, Ganterschwil (CH)

( * ) Notice: Subject to any disclaimer, the term of this patent is extended or adjusted under 35 U.S.C. 154(b) by 0 days.

(21) Appl. No.: 14/901,742

(22) PCT Filed: Jul. 2, 2014

(86) PCT No.: PCT/CH2014/000093
§ 371 (c)(1),
(2) Date: Dec. 29, 2015

(87) PCT Pub. No.: WO2015/000091
PCT Pub. Date: Jan. 8, 2015

(65) Prior Publication Data
US 2016/0151558 A1    Jun. 2, 2016

(30) Foreign Application Priority Data

Jul. 3, 2013   (CH) ..................... 1199/13

(51) Int. Cl.
| A61M 5/00 | (2006.01) |
| G06K 19/077 | (2006.01) |
| A61J 1/18 | (2006.01) |
| A61M 5/315 | (2006.01) |
| G06K 19/07 | (2006.01) |
| G06K 19/073 | (2006.01) |
| G09F 3/02 | (2006.01) |
| A61M 5/50 | (2006.01) |

(52) U.S. Cl.
CPC ............ *A61M 5/002* (2013.01); *A61J 1/18* (2013.01); *A61M 5/31511* (2013.01);
(Continued)

(58) Field of Classification Search
CPC .. A61M 5/002; A61M 2205/3368; A61J 1/18; G06K 19/0717; G06K 19/07345; G06K 19/007705
See application file for complete search history.

(56) References Cited

U.S. PATENT DOCUMENTS

| 7,978,564 B2 * | 7/2011 | De La Huerga .. A61M 5/14212 221/15 |
| 2007/0219503 A1 * | 9/2007 | Loop .................. A61M 5/31511 604/187 |

(Continued)

FOREIGN PATENT DOCUMENTS

| WO | 2006/016343 | 2/2006 |
| WO | 2011/032956 | 3/2011 |

*Primary Examiner* — Thomas Alunkal
(74) *Attorney, Agent, or Firm* — Rankin, Hill & Clark LLP

(57) ABSTRACT

The package for a pharmaceutical product includes a syringe and an electronic tag for obtaining information relating to the integrity of the product as assessed from an exposure of said product to physical or environmental conditions during a time span. The tag is attached at or to a constituent of the syringe; or at least a portion of the tag is integrated in a constituent of the syringe. The tag includes an electronics unit having a control unit, a sensor unit having at least one sensor for monitoring the physical or environmental conditions, a display unit having a display for displaying data relating to the integrity referred to as status data and a switch. The control unit is structured and configured for effecting that the display unit displays the status data in reaction to an operation of the switch.

18 Claims, 5 Drawing Sheets

(52) U.S. Cl.
CPC ....... *A61M 5/5086* (2013.01); *G06K 19/0717* (2013.01); *G06K 19/07345* (2013.01); *G06K 19/07705* (2013.01); *G06K 19/07711* (2013.01); *G06K 19/07798* (2013.01); *G09F 3/02* (2013.01); *A61M 2205/332* (2013.01); *A61M 2205/3327* (2013.01); *A61M 2205/3368* (2013.01); *A61M 2205/6018* (2013.01); *A61M 2205/6027* (2013.01)

(56) References Cited

U.S. PATENT DOCUMENTS

| | | | |
|---|---|---|---|
| 2007/0270744 A1* | 11/2007 | Dacquay | A61F 9/0017 604/114 |
| 2007/0273507 A1 | 11/2007 | Burchell et al. | |
| 2008/0033368 A1* | 2/2008 | Fago | A61M 5/14546 604/189 |
| 2008/0106388 A1* | 5/2008 | Knight | A61M 5/31511 340/10.42 |
| 2008/0125713 A1* | 5/2008 | Nemoto | A61M 5/1456 604/152 |
| 2009/0043253 A1* | 2/2009 | Podaima | G06F 19/322 604/67 |
| 2013/0144206 A1* | 6/2013 | Lee | A61M 5/1723 604/66 |
| 2014/0207099 A1* | 7/2014 | Nagar | A61M 5/14244 604/503 |
| 2014/0249410 A1* | 9/2014 | Uber, III | A61M 5/31573 600/432 |

* cited by examiner

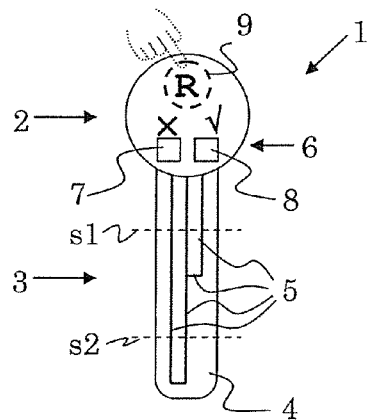
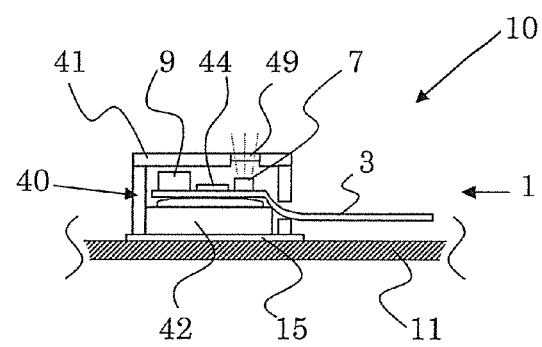
Fig. 1          Fig. 2
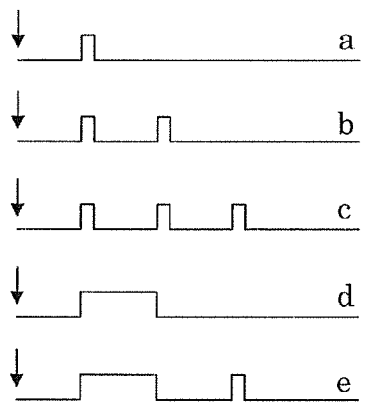
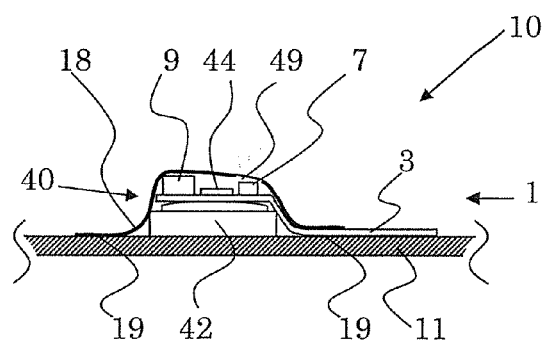
Fig. 5          Fig. 3
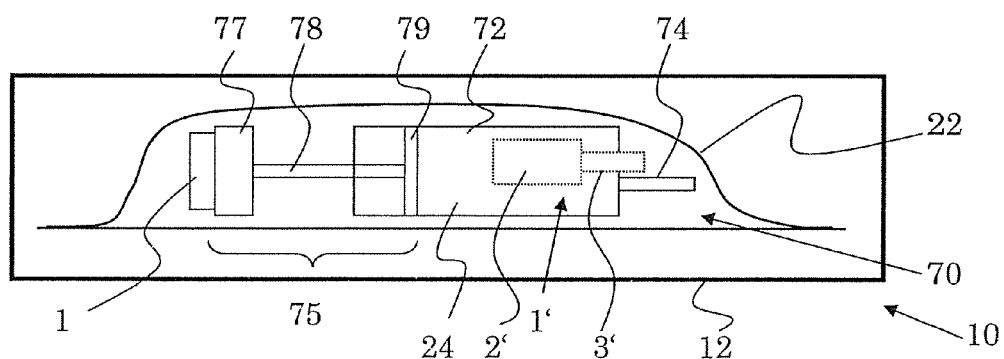
Fig. 4

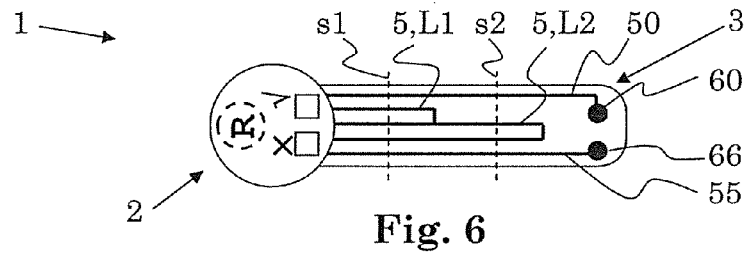
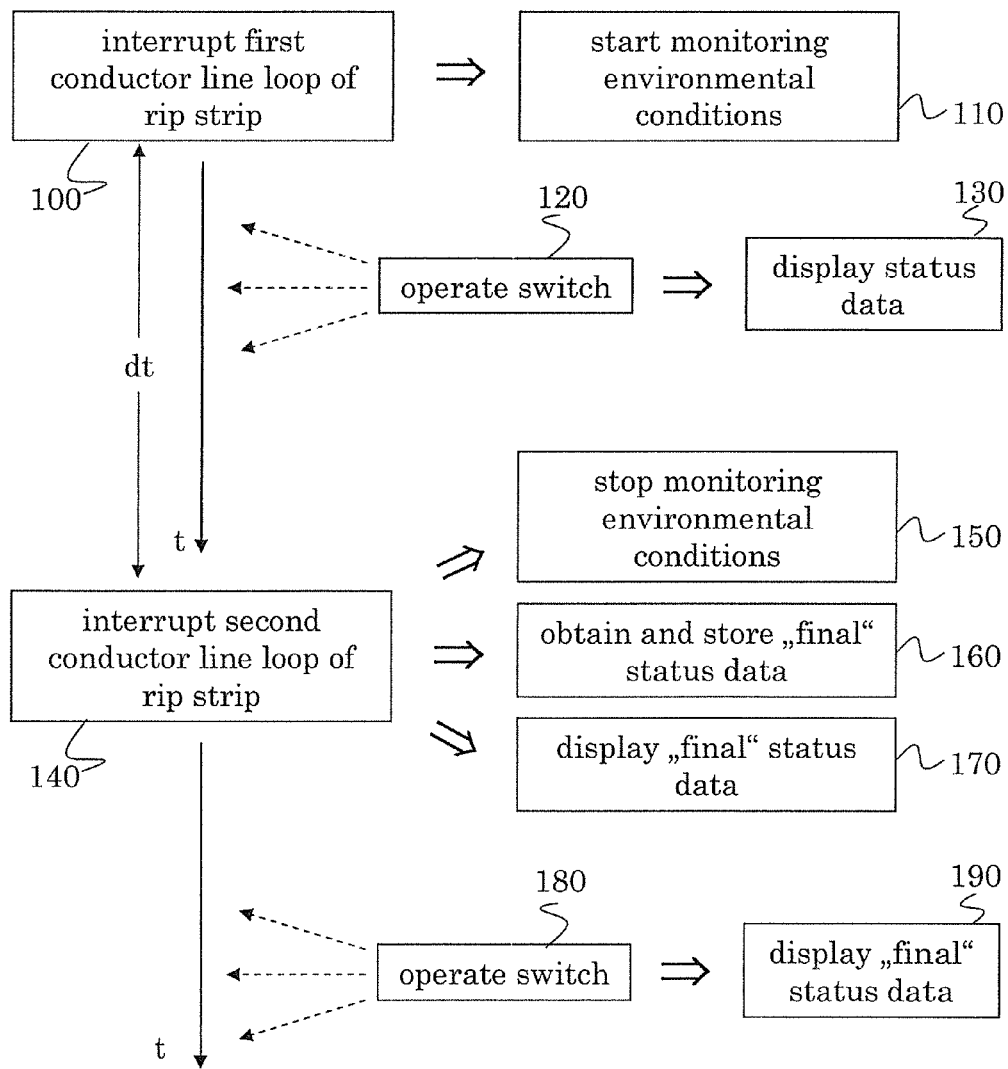
Fig. 6
Fig. 7

MONITORING PRODUCT INTEGRITY OF A PHARMACEUTICAL PRODUCT IN A SYRINGE USING A MINIATURIZED ELECTRONIC SENSOR TAG

BACKGROUND OF THE INVENTION

Field of the Invention

The present invention relates to the field of monitoring the integrity of pharmaceutical products that are sensitive to physical or environmental conditions. More specifically, the present invention relates to the monitoring of the integrity of a pharmaceutical product in a syringe, and moreover relates to ways of estimating the integrity of a pharmaceutical product in a syringe as assessed from the exposure of the product to physical or environmental conditions up to at least approximately the time of its use.

Description of Related Art

When it comes to sensitive or delicate pharmaceutical products, it can be desirable to monitor their exposure to specific hazards such as particularly high or low temperatures, particularly high or low humidity (water-content of ambient air), or particularly strong impacts (hits, blows), so as to be able to estimate the integrity of the transported or stored goods.

It is known to use chemical indicators for estimating the temperature exposure of a medicament. For example, a particular chemical substance is applied onto a syringe containing a pharmaceutical product. If that substance is exposed to a too high or too low temperature during a too long time, its color is (visibly) changed. Corresponding products are commercially available.

Furthermore, RFID tags are frequently used by transport and logistics companies for monitoring the integrity of various goods during their transport from the manufacturer of the goods to a distributor or wholesaler. Such RFID tags are, e.g., attached to a trading unit on a palette, and results of measurements carried out in the RFID tag, e.g., temperature measurements, are wirelessly transmitted to the RFID reader in order to be evaluated and/or looked at.

SUMMARY OF THE INVENTION

One object of the invention is to create a new way of enabling a person using a pharmaceutical product in a syringe such as a health care specialist, to check whether or not the product is—with a high probability—sound, in particular at the time of using the product.

Another object of the invention is to provide a simple way of enabling a person to check the integrity of a pharmaceutical product in a syringe, in particular approximately at the time of its use.

Another object of the invention is to provide a way of enabling a person to check the integrity of a pharmaceutical product in a syringe, in particular approximately at the time of its use, which is compatible with already established packaging and distribution schemes.

Another object of the invention is to provide a way of enabling a person to check the integrity of a pharmaceutical product in a syringe without requiring the presence of any additional object or tool for doing so, e.g., without a reading device.

Another object of the invention is to provide a way of minimizing the probability of fraud or deceit when it comes to proving or demonstrating an integrity status of a pharmaceutical product in a syringe approximately at the time of its use.

Another object of the invention is to provide ways for preventing or reducing malpractice in conjunction with monitoring the integrity of a sensitive pharmaceutical product in a syringe.

Another object of the invention is to provide a particularly cost-effective way monitoring the integrity of a pharmaceutical product in a syringe and/or of enabling a person to check the integrity of a pharmaceutical product in a syringe.

Another object of the invention is to provide a way of manufacturing a package for a pharmaceutical product or of a portion thereof, which has a particularly low number of manufacturing steps.

A corresponding package for a pharmaceutical product as well as a corresponding method for monitoring an integrity of a pharmaceutical product shall be provided. Furthermore a corresponding packaged pharmaceutical product, a corresponding plunger device and a corresponding tag device shall be provided as well as corresponding methods for manufacturing a package for a pharmaceutical product, for manufacturing a tag device, and for manufacturing a plunger device.

Further objects emerge from the description and embodiments below.

At least one of these objects is at least partially achieved by apparatuses and methods according to the patent claims.

According to the present invention, a package for a pharmaceutical product includes:
  a syringe;
  an electronic tag for obtaining information relating to the integrity of the product as assessed from an exposure of the product to physical or environmental conditions during a time span;
wherein
I) the tag is attached at or to a constituent of the syringe; or
II) at least a portion of the tag is integrated in a constituent of the syringe;
and wherein the tag includes an electronics unit including
  a control unit;
  a sensor unit including at least one sensor for monitoring the physical or environmental conditions;
  a display unit including a display for displaying data relating to the integrity referred to as status data;
  a switch;
wherein the control unit is structured and configured for effecting that the display unit displays the status data in reaction to an operation of the switch.

Such a package can make possible that a user who wants to use or apply the pharmaceutical product (who usually is not a person trading it or dealing with it), such as a patient or a health care specialist, can in a simple and direct way and without further education and without needing further equipment or tools operate the tag and find out about the integrity of the pharmaceutical product, in particular at (approximately) the time of using or applying the product. And the package can be very compact and cost-efficient.

The term "package" is used in a rather wide sense, as already the syringe with attached tag is considered a package, since the pharmaceutical product to be contained in the syringe (usually in a barrel of the syringe) can be considered to be packaged thereby. However, as will become clear, the package can also be a package in a narrower and more conventional sense, such as a package including an outer package such as a cardboard box or a polymer blister inside of which the syringe is present.

In the above configuration I), the tag is attached to or at a constituent of the syringe. In this case, the constituent can be a separate part to or at which the tag is fixed, usually by fixing at least a constituent of the tag, such as a housing of the tag, at or to the constituent of the syringe. The attaching may be accomplished, e.g., by means of a bonding agent present between the respective constituent of the syringe and the respective part or constituent of the tag, or by form-fitting, e.g., wherein the part of the tag fully or partially encompasses the respective constituent of the syringe.

Configuration I) can be considered a "retrofit" solution. Configuration I) can allow to use conventional syringes for producing the package.

In the above configuration II), at least a portion of the tag (or a constituent of the tag) is integrated in a constituent of the syringe. This may be accomplished, e.g., by providing that the portion of the tag is contained in the constituent of the syringe, or by providing that the portion of the tag establishes the constituent of the syringe or, vice versa, that the constituent of the syringe establishes a portion of the tag.

More concretely, the electronics unit or a portion thereof may be contained in a constituent of a plunger assembly of the syringe and in particular in a plunger top of the syringe; or a housing of the tag is established by or establishes a constituent of a plunger assembly of the syringe and in particular a plunger top of the syringe. For example, a single injection molded part may house at least a portion of the electronics unit and function as a plunger top of the syringe.

Configuration II) can be considered an "integrated" solution. Configuration II) can allow to minimize the number of assembling steps required for producing the package and/or to minimize the number of parts that have to be produced for producing the package. It may also be possible to reduce the size of the package and/or the amount of material required for producing the package when selecting configuration II).

Further details and possibilities are described below.

As is usually the case for tags for integrity monitoring, it is assumed that the monitored pharmaceutical product is exposed to approximately the same physical or environmental conditions as is the tag.

The time span usually is a time span during which the product is stored or transported.

The switch usually is a user-operable switch, a human-operable switch. Suitable switches can be, e.g., electro-mechanical switches or capacitive switches. These can be particularly cost-effective and very small. However, magnetic switches and inductive switches may be applied, too. The switch may render superfluous the use of (additional or external) tools for receiving information about the integrity of the pharmaceutical product.

The switch may, in particular, be operable by touching it, and/or it may be operable by pressing or pushing it, and/or it may be operable by approaching it, e.g., approaching it to less than 1 cm or less than 4 mm, e.g., in case of a capacitive switch. The touching, pressing, pushing, approaching may be accomplished, e.g., with a finger.

The package may include a pressing surface for operating the syringe by pressing against the pressing surface, wherein the pressing surface is provided by the tag. In case of conventional syringes, the pressing surface is provided by a conventional plunger top. However, providing that the pressing surface is a surface of the tag, it can be achievable to force an operation of the switch (and a displaying of status data) when the syringe is operated, i.e. when at least a portion of the pharmaceutical product is pressed out of the barrel by means of a plunger assembly of the syringe, as is the case when the syringe is used for giving a patient a shot. The pressing surface may be considered a surface provided for reducing a space available in the barrel for the pharmaceutical product by pressing against the surface. Via a plunger rod, a plunger seal will be moved inside the barrel.

The display usually is a visual display.

The displaying of the status data in reaction to an operation of the switch is effected at least after the end of the time span. This can make possible to review the integrity status the product had, e.g., when the syringe was used. It may, however be provided that the displaying the status data in reaction to an operation of the switch is also effected already before the end of the time span, as in the example above. This can make possible early checks of the product integrity, in particular before operating the syringe.

The display does usually not permanently display the status data. This saves energy and thus makes possible a long operation duration of the tag and thus a long shelf life of the package and the tag.

Furthermore, it can be provided that displaying the status data takes place only in reaction to operating the switch. However, it may also be provided that it takes place also in reaction to terminating the monitoring and thus at the end of the time span. (Termination of the monitoring may take place in reaction to breaking a breakable electrical connection described further below and a detection of the breaking.) And alternatively or additionally thereto, it may be provided that displaying the status data takes place periodically, e.g., in regular time intervals, the (pause) interval typically being between 1 second and 2 minutes, in particular between 5 seconds and 30 seconds. Such an "automatic" display of the status data may take place after the end of the time span only or during the time span only or both, i.e. from the beginning of the time span. Looking at the display in the right moment (or waiting for up to once the pause interval) may thus dispense with operating the switch when the integrity status shall be checked. However, the switch may be operated in order to have the status data displayed.

Status data displayed after the monitoring (or measuring, or sensing) has been terminated, i.e. after the end of the time span, may be referred to as "final" status data. In case of final data, all alarms may be indicated which occurred between the initial point in time at which monitoring began and the time of termination of the monitoring. It is furthermore possible to provide that these "final" status data are also displayed (even without operating the switch) when the monitoring is terminated. This makes possible an immediate check of the integrity status. And a calculation and/or a storing step may also take place at that time, so as to obtain these "final" status data and store them in the tag, so as to readily have access to them later on.

If it is provided that status data may be displayed by the display already during the time span, e.g., in reaction to operating the switch, these status data certainly merely reflect those alarm conditions which were met up to that instant.

Furthermore, it is also possible to provide that in addition to displaying status data by means of the display (or as an alternative thereto), status data can be transmitted by the tag via electro-magnetic radiation in the radio-frequency (RF) range (radio-frequency radiation).

In one embodiment, which may be combined with one or more of the before-mentioned embodiments, the tag, in particular the electronics unit, includes an RF receiver and an RF transmitter, or an RF transceiver, and the control unit is structured and configured for effecting that the status data are transmitted using the RF transmitter or the RF transceiver. This transmission of status data may be effected in reaction to an operation of the switch and/or in reaction to receiving, in the tag, a corresponding request signal by means of the RF receiver or RF transceiver. An RF reading device may, this way, receive status data from the tag, in a contact-less fashion. This may be of advantage when a large number of syringes shall be examined with respect to their individual product integrity.

In one embodiment, which may be combined with one or more of the before-mentioned embodiments, the tag includes no RFID (Radio Frequency Identification) responding capability. However, it is, as an alternative also possible to provide that the tag includes RFID responding capability:

In one embodiment which may be combined with one or more of the before-mentioned embodiments except for the last-mentioned one, the tag includes RFID (Radio Frequency Identification) responding capability. For example, the tag (in particular the electronics unit) includes an RF receiver and an RF transmitter, or an RF transceiver. This may allow to identify in a contactless fashion, each individual tag and thus each individual syringe. In this case, each tag may be provided with a unique identifier, which typically would be stored in the electronics unit, and which can be transmitted by the tag via RF, e.g., to an RFID reader. This may allow to achieve a quick overview over a large number of syringes, e.g., in order to check which syringes are present (and thus, which syringes would possibly be missing).

The pharmaceutical product usually is an injectable medicament. It usually is a liquid, e.g., an aqueous solution.

The pharmaceutical product can be, e.g., a synthetic pharmaceutically active substance, a natural pharmaceutically active substance, and in particular a vaccine. Vaccines are often very delicate and also expensive, such that efforts for monitoring the integrity of vaccines in syringes can be particularly useful, in particular when the vaccines are intended for use in subtropical or tropical regions.

The pharmaceutical product can be intended for human use, but it can be also be a pharmaceutical product for use with animals, i.e. a veterinary pharmaceutical product. The invention will mainly be described for the case of pharmaceutical products for human use, but it is readily understood how the invention applies for veterinary pharmaceutical products.

In one embodiment, the syringe includes a barrel and a plunger assembly, and the tag is attached to or at the plunger assembly, more particular to or at a constituent of the plunger assembly. Alternatively, the tag can be attached to or at the barrel. Since the barrel usually is sterilized, an exposure to the sterilization procedure of the tag can be avoided by providing that the tag is attached to or at a constituent of the plunger assembly, in particular to a constituent which is not exposed to the sterilization procedure.

The barrel is provided for containing the pharmaceutical product.

The plunger assembly usually includes a plunger top, a plunger rod, and a plunger seal. The plunger seal (also referred to as "stopper") constitutes one end of the plunger assembly and is provided for providing a seal inside the barrel, so as to allow to move the pharmaceutical product out of the barrel when the plunger assembly is moved during carrying out an injection (giving a shot to a person). The opposite end of the plunger assembly is constituted by the plunger top. In the usual operation of the syringe, the plunger seal is moved by operating, more particularly pressing against, the plunger top, cf. also the pressing surface mentioned above. The two ends of the plunger assembly are interconnected by the plunger rod.

The plunger assembly can be manufactured in a single process, it may constitute a unitary or integrally formed part, e.g., a single molded part. Optionally, a sealing body, e.g., made of a resilient material, can be provided, in addition, in order to establish or contribute to establishing the plunger seal.

However, it is also possible to manufacture the plunger top and the plunger seal separately or to provide them initially as separate parts and interconnect them then. This can be a suitable way of avoiding an exposure of the tag to a sterilization procedure. For example, a fixture is provided between the plunger rod and one or both of plunger top and plunger seal. The fixture may be, e.g., a bonding agent such as a glue, or a pair of corresponding inner and outer threads, or a clamping fixture. Thus, it can be provided that the plunger top is separable from the plunger seal, which can be accomplished, e.g., by providing a separable connection between plunger top and plunger rod and/or between plunger rod and plunger seal.

In one embodiment, which may be combined with the before-mentioned embodiment, the syringe includes a barrel and a plunger assembly includes a plunger top, and I) the tag is attached to or at the plunger top; or II) at least a portion of the tag is integrated in the plunger top.

This may facilitate avoiding an exposure of the tag to a sterilization procedure. For example, attachment of the plunger top to the rest of the syringe (in particular—directly or rather indirectly—to the barrel) may be accomplished after a sterilization procedure has been carried out. Furthermore, in particular for configuration I), the shape or form of the plunger top may be particularly suitable for attaching a tag, in particular a particularly miniscule tag. The tag may have an overall volume of less than three times the volume of a battery comprised in the tag.

In one embodiment referring to the last-mentioned embodiment, the switch is structured and arranged such that operating the syringe effects operating the switch. This way, it can be achieved that the status data are unavoidably displayed when the syringe is operated—at least provided that the syringe is operated in an intended way (which is the usual way of operating the syringe), i.e. involving pushing the plunger top or pressing (directly or indirectly) against the plunger top towards the direction in which the plunger seal is located. Thus, when letting out an amount (usually only a small amount) of the pharmaceutical product out of the barrel prior to giving the shot (which usually is done immediately before giving a shot in order to remove air or other gases possibly present in the barrel together with the pharmaceutical product), the status data are displayed, such that giving the shot with an unsound (perished) pharmaceutical product can be avoided (when paying attention to the display), whereas in case the display indicates (in reaction to operating the syringe) that the pharmaceutical product is assumed to be in order, the shot can be safely given.

When starting to give a shot with the syringe, the process may be interrupted at an early stage when the display indicates that the pharmaceutical product is (according to the monitoring results obtained by the tag) not sound anymore.

The switch may, in particular, be arranged beyond the plunger top, it may be arranged on a side of the plunger top facing away from the plunger rod or the plunger seal.

The tag may have an operation side from which the switch is to be operated, and the operation side may face away from the plunger assembly. This can be the case in particular for electro-mechanic switches and capacitive switches. The tag may be arranged such that its operation side faces away from the plunger rod or the plunger seal.

And the tag may have an operating direction into which the switch is to be operated, the operating direction lying along the operation direction of the syringe, i.e. along the direction pointing along the extension of the plunger rod from the plunger top to the plunger seal. This can be the case in particular for electro-mechanic switches, but, depending on the implementation also for capacitive switches, magnetic switches and inductive switches.

It can, in particular, be provided that the tag includes a printed circuit board (usually a flexible printed circuit board) on which the switch is mounted, and the printed circuit board is located between the switch and the plunger top.

The attaching the tag at or to a constituent of the syringe (cf. configuration I)) can be accomplished by, e.g., bonding, gluing, using a fluidly applicable glue, using a double-faced adhesive tape, using a polymer cover foil sandwiching the tag between itself and the respective constituent of the syringe and including a circumferential portion surrounding the tag, which is bonded to the respective constituent of the syringe, or in another way.

In one embodiment, which may be combined with one or more of the before-mentioned embodiments in which the tag is attached to or at the plunger top, a bonding agent is present between the plunger top and the tag. This way, the tag can be quickly and cost-effectively attached to or at the plunger top. The bonding agent may be a double-sided adhesive tape, but a glue can also be used as the bonding agent.

In one embodiment, which may be combined with one or more of the before-mentioned embodiments in which the tag is attached to or at the plunger top, the tag includes a housing, and at least a portion of the plunger top is contained in the housing. This is another way of attaching the tag or of fixing the tag to the plunger top. In this case, the plunger top is present inside the housing. And this may provide for a mutual fixture of tag and plunger top (or, more generally, of tag and constituent of syringe). An additional bonding agent may be present of not.

In one embodiment, which may be combined with one or more of the before-mentioned embodiments in which configuration II) may apply, the constituent of the syringe constitutes or establishes the at least one portion of the tag. This can enhance manufacturability of the package, e.g., by reducing the number of assembly steps and/or by reducing the number of parts to be manufactured. Two different functions, a tag-related function and a syringe-related function can thus be fulfilled by one and the same item. For example, a portion of a plunger assembly of the syringe may establish a housing of the tag. Furthermore, it may be provided that a portion of the plunger assembly contains a portion of the tag such as the electronics unit or a portion thereof. The portion of the plunger assembly may in particular include the plunger top; it may, e.g., be the plunger top, or it may be a part establishing the plunger top and at least a portion of the plunger rod.

In one embodiment, which may be combined with one or more of the before-mentioned embodiments in which configuration II) may apply, the constituent of the syringe contains the at least one portion of the tag. This may simplify producing the tag and/or reduce the amount of material required for producing the package. The tag or a portion thereof can be at least partially enclosed by the constituent of the syringe. The constituent of the syringe (e.g., a portion of a plunger assembly of the syringe) may establish a housing for the tag or for a portion thereof such as for the electronics unit or a portion thereof. The portion of the plunger assembly may in particular include the plunger top; it may, e.g., be the plunger top, or it may be a part establishing the plunger top and the plunger rod or establishing the plunger top and a portion of the plunger rod.

In one embodiment which may be combined with one or more of the before-mentioned embodiments, the tag includes a housing including a first and a second housing portion, which are mutually attached, in particular they may be establishing a snap fit with one another. This way, e.g., the electronics unit can be readily inserted into the housing. In addition, this may very much facilitate attaching the tag to or at the plunger top. In case the tag includes a rip strip, the housing may include an opening through which the rip strip extends out of the housing. The opening may, in particular, be present at a location where the first and a second housing portions are proximate, e.g., the opening being defined by one or both, the first and the second housing portion. This may facilitate assembling the package.

In particular, it may be provided that the first and second housing portions are interconnected by a folding portion. The folding portion may allow a tilting of the first versus the second housing part, in particular due to a resilience or elasticity of the folding part, wherein this resilience or elasticity may be due to a reduced thickness of the folding portion with respect to adjacent regions of the first and second housing portions. Such a tilting can take place in a well-defined way. Thus, during manufacture and more particularly during mutually attaching the first and second housing portions, no particular positioning or alignment steps have to be carried out and no particular positioning or aligning measures have to be taken in order to ensure a safe and precise fitting together of the first and second housing portions. This greatly facilitates manufacture of the package.

In configuration I), it can, in particular, be provided that the plunger top is contained in the housing (when the first and second housing portions are fixed to each other, i.e. when the snap fit is closed which usually means that the housing is closed). This way, an attaching of the tag to or at the plunger top may be accomplished without the need of providing a bonding agent between tag and plunger top.

In configuration II), it can in particular be provided that the plunger top is established by the housing of the tag. Vice versa, one could say that the tag or a portion thereof is established by the plunger top, because the plunger top establishes the housing of the tag.

The housing may furthermore be one single unitary or integrally formed part. It may be, e.g., one single molded part such as an injection molded part. It can be a continuous part. This can greatly facilitate the manufacture of the package, since less parts need to be manufactured, and less parts need to be assembled. In configuration II), the complete housing of the tag plus the plunger top and optionally also plus the plunger rod (or a portion thereof) may be a single continuous (integrally formed) part, e.g., a single molded part.

In one embodiment referring to the last-mentioned embodiment, the second housing portion has an opening, and a constituent of the plunger assembly, in particular the plunger rod, extends into or through the opening.

Considering Configuration I):

In a first case, the opening is fully or practically fully surrounded by material of the second housing portion. The opening may thus be referred to as a hole. In this case, a mechanical fixation of the tag to the plunger top may be particularly sturdy. However, it will usually be necessary or advisable to provide that the plunger assembly includes separately manufactured parts such as a plunger top being a part manufactured separately from the plunger seal, such that the separately manufactured parts can be assembled later, namely after the opening in the second housing portion has been slid over the plunger rod.

In a second case, the opening is a recess or groove, in particular a recess or groove allowing to sidewise insert the plunger rod into the opening. In this case, a mechanical fixation of the tag to the plunger top may be less sturdy than in the first case (provided other properties remain substantially identical). However, such a design of the second housing portion can make possible to attach the tag while the plunger assembly is attached to the barrel.

Considering Configuration II):

The opening may be fully or practically fully surrounded by material of the second housing portion. The opening may thus be referred to as a hole. The plunger top may constitute a housing of the tag, and a plunger rod may be introduced into the plunger top in order to be fixed to the plunger top there. As an alternative to the opening in the second housing portion in configuration II), the second housing part may provide a protrusion at which or by means of which a plunger rod may be fixed to the plunger top.

In one embodiment, which may be combined with one or more of the before-mentioned embodiments, the tag includes a housing (which may or may not include the first and a second housing portions, cf. above, and may or may not be integrated in the syringe), and the housing includes a flexible portion structured and arranged for interacting with the switch. The flexible portion can be provided for making possible to operate the switch through or across the housing. It can be deformable so as to allow to apply force to the switch via (or through) the flexible portion and/or to approach the switch more closely than without deforming the flexible portion. These properties can be valuable, in particular, in case of electro-mechanical switches and also of capacitive switches.

The flexible portion can be realized by providing a slit in the housing defining the flexible portion. The flexible portion may constitute a tongue in the housing, wherein the tongue substantially is the flexible portion. The tongue has at least one free end. At another end, it usually is continuous with a further part (or with the rest) of the housing.

The flexible portion can furthermore be realized by providing an area of reduced material thickness (nearby the switch). If the thinness of the flexible portion enables a deformation thereof allowing to operate the switch via the flexible portion, a provision of slits in the housing for defining the flexible portion or a tongue may be dispensed with.

It is furthermore possible to provide a housing, which is generally flexible or elastically deformable (e.g., due to material thickness and/or material selection), so as to allow to operate the switch through the housing. In this case, the housing substantially may be identical with the flexible portion.

As an alternative to providing the flexible portion, it is also possible to provide an opening in the housing providing access to the switch. For inductive and for magnetic switches, but also for capacitive switches, it may even be completely dispensed with special provisions concerning shape or material of the housing for facilitating operating the switch.

In case a flexible portion is provided, and the housing includes the above-described first and second housing portions, the second housing portion having the opening, it may in particular be provided that the flexible portion is provided in the first portion.

In one embodiment, which may be combined with one or more of the before-mentioned embodiments, the tag includes a housing (which may or may not include the first and a second housing portions, cf. above, and which may or may not include the flexible portion, cf. above, and which may or may not be integrated in the syringe), and the tag includes a battery, and the housing includes a holder for holding the battery. In the above-described case of a provision of the first and second housing portions, the holder may be provided in the first or in the second or in both, the first and second housing portions.

The holder may, in particular, be or provide a clamping fixture. Clamping the battery in the housing can provide a precise and mechanically sufficiently stable alignment of the battery with respect to the housing—and thus also with respect to features of the housing such as openings or windows (such as windows for light emission). Furthermore, provided that the battery is mounted on a printed circuit board (PCB), e.g., using battery leads, also that PCB and thus also other components mounted on the PCB are aligned with respect to the housing. Typically, a single PCB is provided that is included in the electronics unit and on which also all other components of the electronics unit are mounted such as LEDs or other display components and a controller chip, one or more capacitors and the like. The one PCB may (cf. below) also establish the rip strip, if present.

The holder and/or the clamping fixture may include, e.g., one or more protrusions or ribs present inside the housing.

The battery is usually provided for powering other constituents of the electronics unit.

Instead of a battery, one could also provide a different storage unit for providing electric energy.

In one embodiment, which may be combined with one or more of the before-mentioned embodiments, the tag includes a printed circuit board (PCB) for interconnecting components of the electronics unit. In particular, the PCB is a flexible PCB, e.g., based on a polymer foil. It may be identical with or continuous with a rip strip of the tag (if present).

In one embodiment, which may be combined with one or more of the before-mentioned embodiments, the tag includes a rip strip including a breakable electrical connection operationally connected to the control unit. The rip strip can be used for indicating (to the control unit) the end of the time span, or for indicating (to the control unit) the beginning of the time span, or for both. This may be accomplished, e.g., by suitably cutting the rip strip.

It is usually provided that when the rip strip is ripped (in a suitable place), the electrical connection is broken, e.g., because one or more conductor lines (in particular a conductor line loop) of the rip strip is interrupted. This can be detected by the control unit, e.g., by sensing an increase of an ohmic resistance. It may be an indication of an end of the time span, and thus, the monitoring can be terminated in reaction thereto.

The rip strip usually is a flat member (its extension in a first dimension being clearly smaller than in the other two) and has an elongated shape (its extension in a second dimension being smaller than in the third dimension). The breaking of the electrical connection usually takes place by dividing (cutting, tearing apart) the rip strip generally along the second dimension.

In one embodiment referring to the last-mentioned embodiment, the rip strip includes or essentially is a printed circuit board (PCB). It may, in particular, include or essentially be a flexible printed circuit board. And more particularly it may include or essentially be a foil in and/or on which at least one conductor line is present, which is operationally connected to the control unit. The at least one conductor line forms or establishes the breakable electrical connection and it may, in particular, describe a loop. The foil may, in particular, be an electrically insulating polymer foil. The (usually flexible, but possibly rigid) PCB of the rip strip may be continuous with a PCB of the electronics unit.

It may be provided that the rip strip includes a foil and, present on the foil, at least one conductor line operationally connected to the control unit. In particular, the at least one conductor line may form or establish at least one loop. Typically one or two loops, perhaps three are provided. Each loop may constitute one breakable electrical connection. In case of a single loop, the interruption thereof usually will indicate that the product is about to be accessed and/or indicate that the end of the time span has come (and the monitoring is terminated). In case of two loops, the first is like the before-described single one, and the interruption of the second loop usually will indicate that the product is about to be packaged (or has just been packaged) and/or indicate the beginning of the time span (and thus the start of the monitoring). In case of three loops, yet another functionality may be added to those of the before-described ones.

It is noted that instead of (or in addition to) terminating the time span by ripping a rip strip of the tag, a functionality (provided by the control unit) can be provided that the monitoring is terminated in reaction to an operation of a switch, which we shall refer to as terminating switch. That terminating switch may be identical with or different from the switch ("display switch") for effecting the displaying of the status data (if present). If the switches are identical, different effects may be provoked by differently operating the switch. For example, a brief operation of the switch (e.g., for at most 1 or 1.5 seconds) provokes a displaying of the status data, whereas a longer operation (e.g., for more than 8 seconds) effects a termination of the monitoring. It is furthermore possible to provide a single switch that fulfills at least three different functions accessible by differently operating the switch. These functions may in particular be: starting the monitoring; terminating the monitoring; requesting a displaying of the status data (usually during the whole time span and thereafter, too, namely then displaying the "final" status data, cf. below for details of the "final" status data). The different ways of operating may be operating the switch for time durations in different non-overlapping time duration intervals. For example, operating the switch for less than 2 seconds is interpreted by the control unit as a request for displaying status data, operating the switch for a duration between 3 and 6 seconds is interpreted by the control unit as a request for starting the time span (and thus the monitoring), and operating the switch for more than 9 seconds is interpreted by the control unit as a request for ending the time span and thus terminating the monitoring.

In one embodiment, which may be combined with one or more of the before-mentioned embodiments, the package includes an outer package in which the syringe and the tag are contained. The outer package may be a cardboard box and more particularly a folding carton. It is also possible to provide an outer package substantially made of a polymer, e.g., a blister-type or bag-type polymer package—which usually is air-tight. It is also possible to provide a two-level outer package such as a cardboard box containing a polymer package, e.g., of the before-described kind, which again contains the syringe and the tag.

In one embodiment referring to the last-mentioned embodiment, in the outer package, no further syringe is contained in addition to the before-mentioned syringe.

Similarly:

In one embodiment which may be combined with one or more of the before-mentioned embodiments, the package includes no further syringe in addition to the before-mentioned syringe.

For packages reaching the end user, it is usually meaningful to provide no more than only one single syringe per package. However, one or more additional containers containing further pharmaceutical products such as two vials with different vaccines may be present in the package, too.

In one embodiment which may be combined with one or more of the before-mentioned embodiments, the display unit is structured and configured for displaying the status data by flashing. In other words, the status data are encoded in flashing.

In one embodiment, which may be combined with one or more of the before-mentioned embodiments, the display unit includes one or more light emitters for emitting light pulses, and wherein the data is encoded in a sequence of light pulses emitted by the one or more light emitters. This can allow to realize the tag and thus also the package in a particularly small and particularly cost-efficient way, and it may simplify the manufacture of the tag. The data may more particularly be encoded in one or more of the color of the light pulses;
a duration of the light pulses;
the number of the light pulses in the sequence.

The light emitters may in particular be light emitters for selectively emitting light of at least two different colors. For example, a light source for emitting green light and a light source for emitting red light may be provided.

The light emitters may be, e.g., LEDs (light emitting diodes). LEDs have a low power consumption, which can contribute to a long operating duration of the tag.

Usually, the tag includes merely exactly one display (and not an additional one).

In view of the above-described (and below-described) ways of realizing the display, it is possible to provide that the display is a not-graphical display, at least in the sense that a graphical display would allow to visualize a plurality of different shapes (such as shapes symbolizing letters and/or numbers).

Providing a display of the above-described kind may allow to dispense with graphical displays, at least in the sense that a graphical display, would allow to visualize a plurality of different shapes (such as shapes symbolizing letters and/or numbers).

In one embodiment, which may be combined with one or more of the before-mentioned embodiments, the display automatically displays the status data periodically. The displaying may take place, e.g., in intervals of at least 1 second, more particularly of at least 5 seconds, and/or of at most 2 minutes, more particularly of at most 40 seconds. This may make dealing with the package easier, but usually at the expense of battery power.

In one embodiment, which may be combined with one or more of the before-mentioned embodiments, the control unit is structured and configured for receiving data or signals from the sensor unit, the data or signals being indicative of currently present physical or environmental conditions, and for obtaining the status data from these data or signals. In order to accomplish the latter, the status data are usually obtained in dependence of prescribed limitations for the exposure of the product to the physical or environmental conditions. Those prescribed limitations are usually stored in the tag, in the electronics unit, in form of corresponding data. For example, the control unit usually will compare the current conditions to threshold values such as a value that shall never be exceeded and/or a value that shall never be fallen short of and/or a value that may be exceeded (or fallen short of) only for less than a prescribed time duration. If an alarm condition is met because of extreme values (or extreme values during a too long time duration), it must be assumed that the integrity of the product is not present anymore, i.e. that the product is not in sound condition anymore. This fact can be indicated by the display of the tag, wherein it is possible to provide that different types of alarm conditions are indicated by the display in different ways.

Accordingly, the status data are usually indicative of events (in particular failures) that have occurred after an initial point in time, namely after the moment when the integrity monitoring has started, i.e. after the beginning of the time span. Status data usually reflect only events (in particular failures) that have occurred during the time span. A failure usually is a deviation from or transgression of the above-mentioned prescribed limitations, e.g., an exceeding of a threshold value.

In one embodiment referring to the before-mentioned embodiment, data representative of the prescribed limitations are programmable. Usually, such data are stored in the electronics unit, and in case they are programmable, there is no limitation to one (i.e. to a single) set of such data. This can make possible to use one and the same tag for different products of different sensitivity to the physical or environmental conditions. Thus, it can be sufficient to store only tags of a single type for many different products instead of one type of tag for each type of product.

In one embodiment referring to the before-mentioned embodiment, the tag includes a rip strip (e.g., of an above-described kind) including at least two contact pads (providing electrical contacts), which are operationally (usually electrically and more particularly galvanically) connected to the control unit, and the data representative of the prescribed limitations are programmable by means of signals (usually digital signals) applied to the contact pads.

In a first possibility, it can be provided that one of a plurality of sets of such data representative of the prescribed limitations are selectable by the applied signals. Those sets of data (including at least one value each, such as a maximally allowed temperature) are in this case usually stored in the electronics unit. Accordingly, sufficient memory space for the plurality of data sets is required in the electronics unit. However, programming may be accomplished rather rapidly this way. For example, if a specific type of tag shall be used for monitoring one of various, e.g., twenty, different pharmaceutical products, each having different prescribed limitations, a corresponding number of sets of, e.g., threshold temperatures (and possibly also time durations), may be stored in the electronics unit, and when a specific product shall be monitored, the signals applied to the contact pads allow to select the suitable set of data, such that these are applied in the subsequent monitoring.

In a second possibility, the data representative of the prescribed limitations are entered into the electronics unit by applying the signals. This provides additional flexibility and requires only relatively little storage space in the electronics unit. The programming, however, may be more time consuming than in case of the first possibility.

Referring again to the contact pads, it can be provided that these are arranged in such a location of the rip strip that they are removed from the tag when the rip strip is ripped for indicating that the monitoring shall start, i.e. for indicating the beginning of the time span. As has been described further above, a first and a second loop may be provided, a detection of an interruption of the second loop indicating the beginning of the time span. The contact pads may thus in particular be located, with respect to a coordinate from the control unit along the extension of the rip strip (which usually is a coordinate along the direction of the largest extension of the rip strip), at a location beyond the location of that portion of the second loop which is located farthest along the coordinate. A ripping of the rip strip along a direction approximately perpendicular to the coordinate by which the second loop is opened (interrupted) will thus usually also result in a cutting off of the contact pads from the tag. Attempts to try to program the tag (more particularly, to program data representative of the prescribed limitations) after monitoring has started can be impeded this way.

It is to be noted that, generally, it would also be possible, as an alternative or as an addition to the described programming to tags, to provide a contactless programming, e.g., via electromagnetic radiation. This might, with respect to the above-described provision of contact pads for programming, result in a less time-consuming programming (programming possibly taking place simultaneously with other process steps during packaging) and in higher tag manufacturing costs and possibly also in larger outer dimensions of the tag, more particularly of a main part of the tag.

In one embodiment, which may be combined with one or more of the before-mentioned embodiments, the physical or environmental conditions include a temperature, in particular an ambient temperature.

In one embodiment, which may be combined with one or more of the before-mentioned embodiments, the physical or environmental conditions include a pressure, in particular an ambient pressure.

In one embodiment, which may be combined with one or more of the before-mentioned embodiments, the physical or environmental conditions include a humidity, in particular a relative humidity (water content) of the (ambient) air.

In one embodiment, which may be combined with one or more of the before-mentioned embodiments, the physical or environmental conditions include an acceleration.

In one embodiment, which may be combined with one or more of the before-mentioned embodiments, the sensor unit (and/or the control unit) is structured and configured for measuring the physical or environmental conditions at various times during the time span, in particular in regular intervals.

In one embodiment, which may be combined with one or more of the before-mentioned embodiments, the tag includes a main part including a housing, wherein the housing can in particular be a housing as described further above or below. The housing may be made, e.g., of a polymer, and it may contain the electronics unit. In particular, the housing has an opening through which a rip strip of the tag, if present, extends.

In one embodiment, which may be combined with one or more of the before-mentioned embodiments in which the tag includes a housing, the housing is substantially made of an at least partially transparent material, e.g., a semi-transparent or dull or opaque material.

The packaged pharmaceutical product includes a package according to the invention and the pharmaceutical product, wherein the pharmaceutical product is contained in the syringe.

In the (usual) case that the syringe includes a barrel, the pharmaceutical product is usually contained in the barrel.

The tag device includes:
  a plunger top for use in or with a syringe for applying a pharmaceutical product; and an electronic tag for obtaining information relating to the integrity of a product as assessed from an exposure of the product to physical or environmental conditions during a time span;

wherein

I) the tag is attached at or to the plunger top; or

II) at least a portion of the tag is integrated in the plunger top.

The tag may, in particular, include an electronics unit including:

a control unit;

a sensor unit including at least one sensor for monitoring the physical or environmental conditions;

More specifically, the electronics unit may include:

a display unit including a display for displaying data relating to the integrity referred to as status data;

a switch;

wherein the control unit is structured and configured for effecting that the display unit displays the status data in reaction to an operation of the switch.

The pharmaceutical product, the integrity of which is monitored by the tag, is the pharmaceutical product to be contained in the syringe.

The tag may be a tag having properties of tags described elsewhere herein. In particular, the tag may include a housing, and the plunger top may be contained, at least in part, in the housing.

The tag device may also include a plunger rod integrally formed with or fixed to the plunger top. In this case, and when the tag includes a housing, the housing may, in configuration I), have an opening through which the plunger rod extends, and the opening may be the opening described further above or below in the present patent application. In the configuration II), the tag device may include a plunger rod integrally formed with the plunger top.

The tag device according to the invention may be a portion of the package according to the invention. Accordingly, it may be referred to the description of the package for further details and properties of the constituents of the tag device. For example, the tag may have a rip strip; a housing of the tag may provide a holder or fixture for a battery of the tag; and so on.

The plunger device includes a plunger top for use in or with a syringe for applying a pharmaceutical product, wherein the plunger top establishes a housing. In other words, the plunger top at least partially encloses a hollow. In particular, the housing is suitable for uptake of a part insertable into the housing and into the hollow, respectively. That hollow and thus the housing can, in particular, be suitable for receiving at least a portion of an electronic tag for obtaining information relating to the integrity of a product as assessed from an exposure of the product to physical or environmental conditions during a time span; in particular, the housing is suitable for receiving at least a portion of an electronics unit of the electronic tag, more particularly wherein the portion of an electronics unit includes a battery. The plunger device may furthermore include a plunger rod fixed at or integrally formed with the plunger top; plunger top and plunger rod may be one single molded part, e.g., injection molded part. The housing and the tag may each have properties as described for housing and tags, respectively, described elsewhere herein. In particular, the housing may include a first and a second housing portion interconnected by a folding portion of the housing, wherein the first and a second housing portions are foldable so as to provide a hollow inside of which space is provided which is suitable for uptake of the portion of the electronic tag.

The method for monitoring an integrity of a pharmaceutical product includes the steps of:

a) providing a syringe;

b) providing

I) an electronic tag attached at or to a constituent of the syringe; or

II) an electronic tag at least a portion of which is integrated in a constituent of the syringe;

the syringe including a barrel, the barrel containing the pharmaceutical product;

the tag being a tag for obtaining information relating to the integrity of the product as assessed from an exposure of the product to physical or environmental conditions during a time span, the tag including an electronics unit including:

a control unit;

a sensor unit including at least one sensor for monitoring the physical or environmental conditions;

a display unit including a display for displaying data relating to the integrity referred to as status data;

a switch;

wherein the control unit is structured and configured for effecting that the display unit displays the status data in reaction to an operation of the switch.

The tag and the syringe may have properties as described elsewhere herein for tags and syringes, respectively.

The method may furthermore include the step of c) starting the time span.

Step c) may be accomplished, e.g., by breaking a breakable electrical connection of the tag such as the one described for the rip strip the tag may comprise. In this case, step c) may be caused by ripping the rip strip of the tag.

The method may furthermore include programming prescribed limitations as has been described above, e.g., by applying signals to the control unit, e.g., via at least two contact pads which may in particular be provided by a rip strip of the tag.

Provided the tag includes a rip strip, the method may also include the step of ripping the rip strip. The ripping of the rip strip may be accomplished for terminating the integrity monitoring (and ending the time span).

The method may furthermore include the step of operating the switch. The step of operating the switch may be accomplished for requesting a displaying of the status data.

The method may furthermore include the step of:

by means of the sensor, creating data or signals representative of the physical or environmental conditions at various times during the time span.

The method may furthermore include the step of inserting the pharmaceutical product into the syringe, more particularly into a barrel of the syringe.

Provided that the syringe includes a plunger assembly including a plunger top, the method may include the step of:

d) attaching (or fixing) the tag to or at the plunger top.

This can, in particular, be the case in configuration I).

Step d) may be accomplished by closing a housing of the tag. The housing may have properties of a housing as described elsewhere herein. For example, step d) may be accomplished by folding two portions of the housing, such as by closing a snap fit between two housing halves.

Alternatively, step d) may include interconnecting the tag and the plunger top by and via a double-sided adhesive tape or by some other bonding agent.

The method for manufacturing a package for a pharmaceutical product includes the steps of:

A) providing at least one constituent of a syringe for applying the pharmaceutical product;

B) providing an electronic tag for obtaining information relating to the integrity of the product as assessed from an exposure of the product to physical or environmental conditions during a time span;
the method further including the step of:
CI) attaching the tag to the at least one constituent of the syringe;
or the step of
CII) integrating at least a portion of the tag in a constituent of the syringe.

The tag may be a tag having properties as described for a tag described elsewhere herein. And the same applies to the syringe and to the constituent of the syringe.

The method may in particular include the step of manufacturing a unitary or an integrally formed part, which establishes a housing for at least a part of the tag and a constituent of the syringe. More particularly, the unitary or integrally formed part may establish a housing for at least a part of the tag, e.g., for at least a portion of an electronics unit of the tag, and also a constituent of a plunger assembly of the syringe. The housing may be openable, e.g., including a first and a second housing portion as described above, and the method may include the step of inserting the part of the tag into the housing. Furthermore, the step of closing the housing may be carried out.

This way, an integrated tag (integrated in a syringe) may be realized by producing the unitary or an integrally formed part and inserting the tag (or a portion thereof) in the housing established by that part and closing the unitary or an integrally formed part. Compared to manufacturing a conventional package or syringe, mainly those two steps of inserting and closing add up, besides the costs for producing the tag (or rather for an electronics unit of the tag). A mold for molding the unitary or integrally formed part will usually be more complicated than in case of a mold merely for a conventional syringe. A single injection-molded part may constitute as the unitary or integrally formed part, e.g., the tag housing, the plunger top and possibly also the plunger rod (or a portion thereof).

Provided the syringe includes a plunger assembly including a plunger top, the method may include the step of:
E) inserting at least a portion of the tag, e.g., the electronics unit, into a housing established by the plunger top.

The method for manufacturing a plunger device for use in or with a syringe for applying a pharmaceutical product includes the step of:
K) providing a plunger top, which establishes a housing.

More specifically, the plunger top may at least partially enclose a hollow, more particularly a hollow for uptake of a part insertable into the hollow.

In particular, the housing is suitable for receiving at least a portion of an electronic tag for obtaining information relating to the integrity of a product as assessed from an exposure of the product to physical or environmental conditions during a time span.

Furthermore, the plunger top may be an integrally formed part such as a molded part, e.g., an injection molded part.

The method may, accordingly, include the step of:
L) manufacturing the plunger top using a molding technique.

The housing may have properties as described for a housing described elsewhere herein.

Furthermore, the plunger top may be integrally formed with a plunger rod or a portion of a plunger rod.

The method may, accordingly, include the step of:
M) manufacturing the plunger top integrally formed with at least a portion of a plunger rod.

Step M) may be accomplished using a molding technique.

The method for manufacturing a tag device for use in or with a syringe for applying a pharmaceutical product includes, in a first configuration, the steps of:
QI) providing a plunger top;
RI) attaching an electronic tag to the plunger top; or
or, in a second configuration, the steps of
QII) providing a plunger top, which establishes a housing;
RII) inserting into the housing at least a portion of an electronic tag.

In particular, the tag can be an electronic tag for obtaining information relating to the integrity of the pharmaceutical product as assessed from an exposure of the product to physical or environmental conditions during a time span.

The housing, the tag, the syringe and the plunger top may have properties as described for the respective items elsewhere in the present patent application. For example, step RI) may be accomplished using a double-sided adhesive tape. And the housing may be foldable. And the housing may have two housing portions establishing a snap fit. And the housing may establish a holder for a battery (of the tag).

The method may furthermore include the step of:
S) closing the housing (with at least the portion of the tag inside the housing).

The method may also include the step of:
T) clamping a battery of the tag inside the housing.

In the method, it may be provided that the plunger top is fixed to or integrally formed with at least a portion of a plunger rod.

The method may, in the second configuration also include the step of:
L) manufacturing the plunger top using a molding technique.

And, in the second configuration, the method may include the step of:
M) manufacturing the plunger top integrally formed with at least a portion of a plunger rod.

As mentioned above, step M) may be accomplished using a molding technique.

In a particular view of the invention, some properties of the tag are optional (but may, however, be nevertheless be provided), and at least a portion of the tag is integrated in a constituent of the syringe. In this case, the package for a pharmaceutical product includes:
    a syringe;
    an electronic tag for obtaining information relating to the integrity of the product as assessed from an exposure of the product to physical or environmental conditions during a time span;
wherein at least a portion of the tag is integrated in a constituent of the syringe.

The tag may, more particularly, include an electronics unit including:
    a control unit;
    a sensor unit including at least one sensor for monitoring the physical or environmental conditions.

And it may, as another option, also include:
    a display unit including a display for displaying data relating to the integrity referred to as status data; and
    a switch;
wherein the control unit is structured and configured for effecting that the display unit displays the status data in reaction to an operation of the switch.

Generally, further options and embodiments concerning this particular view of the invention can be derived from the description above and below. This concerns also the methods (monitoring methods, manufacturing methods) and the packaged pharmaceutical product and other devices. In particular, the integration of at least a part of the tag in a constituent of the syringe may mean that a housing of the tag establishes a constituent of the plunger assembly of the syringe and in particular of a plunger top of the syringe.

It is readily understood that features mentioned with respect to a certain portion of the invention, e.g., for a manufacturing method or for a device, can be provided—as far as logically meaningful and at least in analogy—in other portions of the invention, e.g., in a package or in a monitoring method. The achievable effects correspond to each other.

The advantages of the methods basically correspond to the advantages of corresponding apparatuses and vice versa.

Further embodiments and advantages emerge from the dependent claims and the figures.

BRIEF DESCRIPTION OF THE DRAWINGS

Below, the invention is described in more detail by means of examples and the included drawings. The figures show schematically:

FIG. 1 a top view onto an electronic tag;
FIG. 2 a cross-sectional view of an attached electronic tag;
FIG. 3 a cross-sectional view of an attached electronic tag;
FIG. 4 a symbolic cross-sectional view of a package;
FIG. 5 an illustration of sequences of light pulses emittable by an electronic tag;
FIG. 6 a top view onto an electronic tag;
FIG. 7 an illustration of method steps.

DETAILED DESCRIPTION OF THE INVENTION

Figure 8:
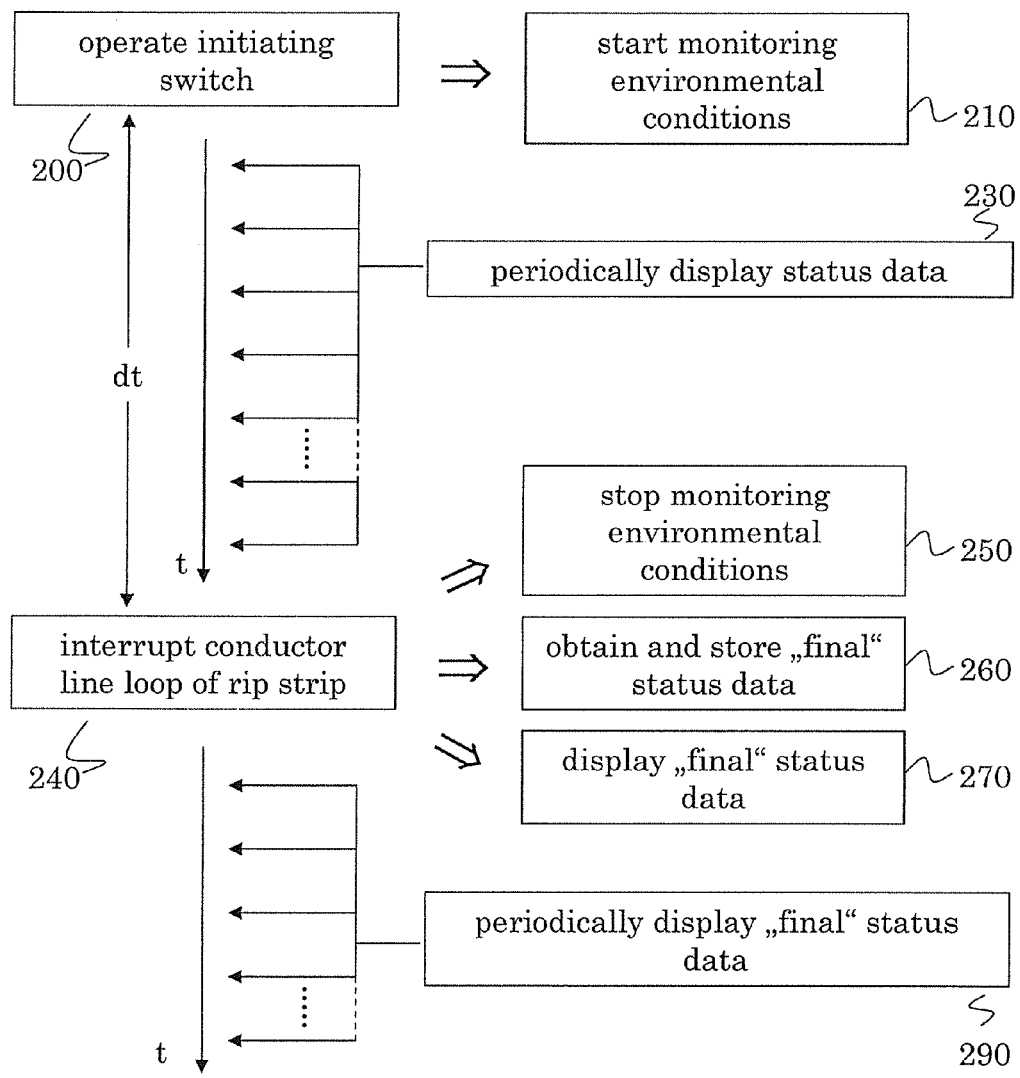
FIG. 8 an illustration of method steps.

The described embodiments are meant as examples and shall not limit the invention.

FIG. 1 shows a schematized top view onto an electronic tag 1. Tag 1 includes a temperature sensor or a sensor for some other physical or environmental condition. The tag can monitor that magnitude and decide whether or not certain (prescribed) conditions concerning that magnitude are met, e.g., whether or not a threshold value has been exceeded and possibly also for how long it has been exceeded. Depending on the monitored (sensed or measured) values (of temperature, pressure, humidity, acceleration or others and usually also of the time), one or more types of alarm indications can be provided by the tag, depending on the type of event or failure that occurred. Since such functionalities are known from prior art, we will not go into much detail here concerning this point.

Tag 1 of FIG. 1 includes a main part 2 and a rip strip 3, which are mutually interconnected. The main part 2 typically has a volume of at most 35 mm×30 mm×12 mm, in particular having a side length of, at most, the specified lengths, and more particularly, it may have a volume of at most 25 mm×20 mm×10 mm, and in particular a side length of, at most, the specified lengths.

The main part 2 includes an electronics unit including i.a. a user-operable switch 9 (cf. the dotted hand symbol in FIG. 1) and a display 6 substantially consisting of two light emitters 7, 8 such as two LEDs, in particular a red LED and a green LED. The rip strip 3 substantially consists of a printed circuit board (PCB) or of a piece or part thereof and more particularly of PCB base material 4 in and/or on which conductor lines 5 are present. It is particularly suitable to provide, as the rip strip 3, an electrically insulating foil 4 such as a polymer foil provided with conductor lines 5.

In fact, the electronics unit (having reference symbol 40 in further figures) and the rip strip 3 may be considered to share one printed circuit board. And the electronics unit 40 may be considered to be a printed circuit board assembly (PCB assembly or PCBA), i.e. a PCB with components mounted thereon (the components being described above and also below), wherein the PCB forming the rip strip 3 is continuous with the PCB of the PCBA representing the electronics unit 40.

FIG. 2 shows a schematic cross-sectional view of an attached electronic tag 1, and at the same time, FIG. 2 may be interpreted to show a schematized detail of a package 10 including a syringe (the syringe bearing reference numeral 70 in further figures). The tag 1 of FIG. 2 may be identical with the one of FIG. 1.

Tag 1 includes electronics unit 40 in its main part 2 and rip strip 3, each including a portion of one and the same PCB, which may be a flexible PCB.

Tag 1 and, more particularly, main part 2 includes a housing 41 in which electronics unit 40 is present. Electronics unit 40 includes, besides the PCB and mounted thereon, an energy source such as a battery 42, the above-mentioned switch 9, which may be, e.g., an electro-mechanical switch or a capacitive switch, the light emitters of the display (only LED 7 being illustrated in FIG. 2) and an integrated circuit (IC) 44 such as an ASIC (application-specific IC). IC 44 may embody a control unit and a sensor unit, but it is also possible that a separate sensor unit is mounted on the PCB.

It is possible that data sensed by a sensor of the sensing unit are continuously (or quasi-continuously) taken, but usually, measuring or sensing takes place in time intervals of between 30 seconds and 12 hours, more particularly between 1 minute and 30 minutes, so as to save energy.

Housing 41 may be made substantially of a material which is sufficiently transparent for letting light emitted by light emitters 7, 8 of tag 1 pass through such that it is visible from the outside, or may include, as indicated in FIG. 2, a transparent or (particularly) thin portion 49 for that purpose.

In order to attach tag 1 to a tag carrier 11 such as a constituent of a syringe, e.g., a plunger top, a double-faced adhesive tape 15 may be used. An alternative would be to use a different bonding technique such as the application of an initially liquid bonding material such as a glue. A bonding may take place between the housing 41 and the tag carrier 11, and it is possible, as indicated in FIG. 2, to provide that it takes place, in addition, between the battery 42 and the tag carrier 11. In the latter case, the adhesive tape 15 or other bonding material may function as a part of the housing of the tag 1.

An alternative way of attaching tag 1 to a tag carrier 11 is illustrated in FIG. 3. In the embodiment of FIG. 3, the tag may be identical with the one of FIG. 1, and its electronics unit 40 may be identical with the one of FIG. 2. However, the attaching of main part 2 to tag carrier 11 is accomplished in an indirect way. More specifically: A foil 18 such as a polymer foil holds main part 2 between itself and tag carrier 11. In an area partially surrounding main part 2, foil 18 is bonded to tag carrier 11 using a bonding material such as a glue (indicated at 19 in FIG. 3, but not separately drawn). Thus, main part 2 is sandwiched between foil 18 and tag carrier 11.

Suitable tag carriers 11 are constituents of a syringe to be provided with a tag, e.g., the barrel of the syringe or a constituent of the plunger arrangement of the syringe. Below, a plunger top will be described as a possible tag carrier, but also a barrel of a syringe will be described as a possible tag carrier.

A pharmaceutical product (later referenced by reference numeral 24) to be monitored by means of the tag is contained in the syringe, more particularly in a barrel of the syringe. The pharmaceutical product usually will be provided in liquid form, so as to be injectable using the syringe.

FIG. 4 is a symbolic cross-sectional view of a two-level package 10 and of a corresponding packaged pharmaceutical product 24. Pharmaceutical product 24 is contained in a barrel 72 of syringe 70. Syringe 70 includes barrel 72 and needle hub 74 (also referred to as adaptor) and plunger assembly 75. Plunger assembly 75 includes plunger seal 79 and plunger rod 78 and plunger top 77.

Syringe 70 is contained in a blister-type package 22 usually made of a polymer (and possible also paper-type material) which again is contained in a box 12, which typically is a folding carton. Instead of such a two-level package 10, also a single-level package might be used for packaging product 24, e.g., providing box 12 only (and no blister-type bag) and providing a blister-type package 22 only (and no additional box).

Whatever constitutes the outer-most package level (in FIG. 4 it is box 12) intended for the end-user (typically patient or health care professional), it may be provided that therein, no further syringe but one single syringe is present. For example, in a folding carton, one syringe (and not more than one) may be present, however, it is possible that, in addition, one or two or more containers each containing another pharmaceutical product are present inside the folding carton, e.g., one or more vials. This may, in particular, be useful in case that the pharmaceutical products are vaccines (such as different vaccines for a single person/patient).

It is to be noted that it is possible that inside a package, e.g., inside a folding carton or a blister-type package, two or more parts (or constituents) of the syringe are separate, i.e. disassembled. In particular, the plunger top (including the tag) and the plunger rod (or a portion of the plunger rod) may be one part which is separate from another part which establishes the barrel and the plunger seal (and possibly also a portion of the plunger rod). Before use, the syringe then has to be assembled from the separate parts.

Providing a disassembled syringe can allow to package the syringe (including the tag) in a smaller outer package, e.g., a smaller folding carton. And an accidental pressing of the pharmaceutical product out of the barrel may be largely inhibited.

A tag 1, e.g., a tag like described elsewhere in the present patent application, e.g., in FIG. 1 or 2, is attached to syringe 70 and more particularly to plunger top 77. As indicated by dotted lines, it is also possible to provide another tag 1' (which includes a main part 2' and a rip strip 3') at a different constituent of syringe 70, e.g., as illustrated, at barrel 72. In particular, it may be provided that in one folding box (such as folding box 12 in FIG. 4), exactly one syringe is present (and no further syringe).

Bag 22 is a container which usually is at least partially constituted by a polymer foil, in particular by transparent polymer foil.

A tag 1, e.g., one as described above, and, more particularly, the corresponding electronics unit 40 can be structured and configured for detecting an interruption of a conductor line loop of rip strip 3, e.g., by cutting rip strip 3 using a cutting tool or by ripping rip strip 3 by hand. And, moreover, this may result in a termination of the monitoring (and of the measurements and of the sensing) being accomplished (or at least evaluated) by the tag 1.

Accordingly, it can be provided that monitoring the integrity of a product 24 is carried out from a starting event to an end point. The starting event can be, e.g., when syringe 70 is packaged in an outer package (in particular into a folding box), or when syringe 70 is assembled (with product 24 in barrel 72), or when product 24 is filled into barrel 72. The end point may be indicated by a ripping of rip strip 3. And this ripping can be linked to an accessing of product 24, e.g., by prescribing (to a user such as a patient or a health care specialist) that rip strip 3 has to be ripped when box 12 is opened or when the syringe is about to be used (for giving a shot). This way, it can be ensured to some extent that the monitoring of the integrity of product 24 is terminated when product 24 is accessed. The integrity status of product 24 may, also in reaction to the ripping, be stored in tag 1 such that it can be recalled later (namely by operating switch 9, cf. FIGS. 1-3) and/or may be displayed by the display 6 of tag 1, e.g., by the emission of light pulses.

A beginning of the time span during which the physical or environmental conditions are monitored may be indicted by breaking another loop present on rip strip 3, cf. also FIG. 7 below. For example, dividing the rip strip of FIG. 1 along the dashed line s2 (and thus opening the longer one of the two loops present on rip strip 3) may be detected by electronics unit 40 (and more particularly by a control unit realized therein) by an increase of an ohmic resistance and make the electronics unit 40 start the monitoring. On the other hand, dividing the rip strip of FIG. 1 along the dashed line s1 (and thus opening the shorter one of the two loops present on rip strip 3; the longer one being already open) may be detected by electronics unit 40 (and more particularly by a control unit realized therein) by an increase of an ohmic resistance and make the electronics unit 40 terminate (stop) the monitoring.

Alternatively, the monitoring can be started differently, cf. below at the description of FIG. 8 ("initiating switch"). In that case, a single conductor line loop may be sufficient, and rip strip 3 may remain unripped at least until after packaging, i.e. at least up to forwarding/shipping the packaged pharmaceutical product 24. Furthermore, rip strip 3 (cf. FIG. 6) might in general be dispensed with. In that case, the tag is substantially identical with its main part.

As is clear from the above, a display 6 of a tag 1 may include (an in particular essentially consist of) one or more light emitters such as LEDs, in particular light emitters of different color, e.g., one emitting red light and another emitting green light. A control unit of tag 1, e.g., an integrated circuit, e.g., the one of FIGS. 2, 3, may control the display 6 to emit light pulses, more particularly sequences of light pulses (wherein already a single light pulse shall be considered a sequence of light pulses). Emitted light pulses in a sequence may differ in at least one of color, duration, intensity. Assuming that color is a parameter which can be varied for displaying integrity status information, generally, the emission of green light may be emitted in order to indicate that the product integrity is still in order, and the emission of red light may be emitted in order to indicate that the product integrity is not in order anymore.

Assuming that in addition, the duration (of a pulse in a sequence) is a parameters which can be varied for displaying integrity status information, it can be provided, e.g., that two or more types of alarm (or types of failures) are indicated by different pulse durations. An example will be illustrated and described by means of FIG. 5.

FIG. 5 is an illustration of sequences of light pulses emittable by an electronic tag 1 such as by an above-described tag 1. The curves "a" to "e" illustrate different sequence which may be emitted in 5 different cases, i.e. in five different integrity statuses. The horizontal axis is the time axis, the vertical axis is the light intensity axis, intensities being either zero or a maximum value.

One way of distinguishing three types of failures (one, two or three of which may have occurred and thus may have to be indicated when displaying the integrity status) works as follows:

If a failure of a first type has occurred, a single short red pulse is emitted (cf. curve a).

If a failure of a second type has occurred, a two short red pulses are emitted (cf. curve b).

If failures of both, first and second type, have occurred, a three short red pulses are emitted (cf. curve c).

If a failure of a third type has occurred, a single long red pulse is emitted (cf. curve d).

If, in addition to a failure of the third type, a failure of the first and/or a failure of the second type has occurred, the (partial) sequence for the additional failure(s) is appended to the long red light pulse indicating the third type failure. Curve e indicates the case that a failure of a first type and a failure of a third type have occurred.

A failure of first type may mean, e.g., that an upper temperature limit T(up) has been exceeded.

A failure of second type may mean, e.g., that a lower temperature limit T(low) has been fallen short of A failure of third type may mean, e.g., that a threshold temperature limit T(thr) has been exceeded (or fallen short of) for a too long time, more particularly for more than a prescribed threshold time t(thr).

Such a kind of data indicative of prescribed limitations of a product, e.g., T(up), T(low), T(thr) and t(thr), are usually stored in the electronics unit. They may be programmable in a way described further above in the present patent application. If programming pads are provided for programming such values, these may in particular be provided on the rip strip. FIG. 6 illustrates a possible design of a rip strip with contact pads for programming such values.

FIG. 6 shows an illustration of a top view onto an electronic tag 1. This tag 1 can be largely identical with other tags described in the present patent application, such as tag 1 of FIG. 1, but the rip strip 3 is designed to provide two contact pads 60, 66. While conductor lines 5 form two loops L1, L2 which may (as illustrated) partially overlap and are readily interrupted by ripping rip strip 3 along separation lines s1, s2, conductor line 50 provides an electrical connection between pad 60 and the electronics unit of tag 1, and conductor line 55 provides an electrical connection between pad 66 and the electronics unit of tag 1. Via contact pads 60, 66, data indicative of prescribed limitations of a product to be monitored (such as the above-mentioned T(up), T(low), T(thr) and t(thr)) may be programmed before ripping rip strip 3 along s1 or s2.

In the process of packaging pharmaceutical products, a (high) number of such tags 1 may be present, and an arbitrary one of them is selected for the next product, and then—when the type of product to be packaged is known—the data indicative of prescribed limitations of that specific product for the exposure of that specific product to the monitored physical or environmental conditions are programmed (using pads 60 and 66). This way, in a single packaging line, the provision of a single type of tag 1 can be sufficient for packaging (and monitoring) in that packaging line a plurality of different products (with different prescribed limitations). Accordingly, storing various different types of tags, each specifically designed for the different products to be packaged (set to the respective specific prescribed limitations for the exposure of the product to the physical or environmental conditions), may become superfluous this way.

And starting the monitoring by opening loop L2, e.g., by cutting along line s2, will simultaneously make a reprogramming of tag 1 difficult, thus impeding tampering with the tag.

If product integrity is in order, this may be indicated by one or more green light pulses. It is, more specifically, possible to distinguish different types of (still-)in-order statuses. For example, in a first case, a single green pulse is emitted, cf., e.g., curve a or curve e. And in a second case, two green pulses are emitted, cf., e.g., curve b, or more than two pulses are emitted, or green and red pulses are emitted.

The first (still-)in-order status case may be, e.g., that no threshold value has been reached. In case a temperature is monitored, this would be the case, e.g., if the temperature never left the range at which the product may be kept virtually forever or (as more often will be the case) until its expiration date.

The second (still-)in-order status case may be, e.g., that for more than a pre-selected time duration, a threshold value has been exceeded and fallen short of, respectively, (depending on the threshold being an upper and a lower threshold value, respectively). For example, in case a temperature is monitored, this would be the case, e.g., if the temperature of the product may be above an upper threshold of, e.g., 37° C. for at most, e.g., 72 hours, and an alarm is desired as soon as only 24 hours or less are left (24 hours being the pre-selected time duration). If then the temperature has in fact been above 37° C. for already more than 48 hours, such that the product will be in order for only less than 24 hours (provided that its temperature will remain above 37° C.), the second (still-)in-order status shall be indicated.

FIG. 7 illustrates method steps. Reference symbol t denotes the time, dt denotes the time span during which monitoring takes place. In steps 100, 110, the time span during which integrity monitoring shall take place is started by interrupting a first electrical contact, e.g., by opening a conductor line loop, cf. also dashed line s2 in FIG. 1. Operating switch 9 during the subsequent time span (step 120) results in a displaying of the status data (step 130).

Interrupting another electrical contact (cf. step 140) results in terminating the time span and the monitoring (step 150), obtaining the final status data (step 160) and displaying the final status data (step 170). When later on, switch 9 is operated (step 180), the final status data are displayed (step 190).

It is to be noted that usually, the status data will not be permanently displayed, but only when the switch 9 is operated; and optionally also when the time span (and thus the monitoring) is terminated and/or optionally in (regular) time intervals (controlled by the control unit), the time intervals being usually between 1 second and 2 minutes, more particularly between 10 seconds and 1 minute.

FIG. 8 is another illustration of method steps, similar to the one of FIG. 7. It illustrates an example for the case that no switch is required for displaying the status data. Instead, the status data are displayed periodically, before and after terminating the monitoring, cf. steps 230 and 290. And FIG. 8 also illustrates an example for the case that monitoring is started without needing a rip strip for that purpose. Instead, the monitoring is started in reaction to the operation of a switch, referred to as initiating switch, cf. step 200. It can be referred to FIG. 2 for illustrating a corresponding electronic tag 1, wherein the item referenced 9 in this case is interpreted as such an initiating switch, i.e. as a switch, when operated, effecting that the monitoring starts. Such a switch may be an electro-mechanical switch, a capacitive switch, a magnetic switch or an inductive switch. Note that it is possible to nevertheless provide in this case a rip strip—in particular for the purpose of terminating the monitoring. But alternatives thereto are possible, e.g., a switch (e.g., the before-mentioned initiating switch) may be provided for that purpose.

Otherwise, the method and the corresponding package and tag may be as described elsewhere herein.

Note that the initiating switch may in particular be a magnetic or inductive switch. For example, the manufacturing of the retail package or retail unit may include moving the same along a path along which a suitable magnet (permanent or electromagnet) and a suitable coil, respectively, is suitably positioned, e.g., along a path described by a conveyor transporting the retail package or retail unit. Then, while passing along the respective magnetic or electric field, the initiating switch is operated (without mechanically contacting the tag), and the monitoring starts. However, the initiating switch might also be an electro-mechanical or a capacitive switch, the latter also allowing a contact-free operation.

Of course, it is also possible to provide in the embodiment of FIG. 8 the before-described switch by means of which a displaying of the status data can be initiated (display switch). This switch (sufficiently described above) may be identical with the initiating switch or be an additional switch. In case the switches are identical, it may be provided that different effects may be provoked by differently operating the switch. For example, a brief operation of the switch (e.g., for at most 1.5 seconds) provokes a displaying of the status data, whereas a longer operation (e.g., for at least 3 seconds) can effect that the monitoring starts. Moreover, the function of the rip strip (for terminating the monitoring) may also be assumed by the switch, e.g., termination of monitoring is in that case effected in reaction to operating the switch for an even longer time (e.g., for at least 8 seconds). In this case, the rip strip may be dispensed with.

Instead of bonding the tag 1 to a part of the syringe 70, tag 1 can be attached thereto in a different manner or even be integrated, at least in part, therein. The following examples basically refer to the plunger top as a syringe constituent to or at which the tag is attached or in which a part of the tag, such as in particular a housing of the tag, is integrated. But other constituents of the syringe may also be used for attaching or integrating the tag.

Figure 9:
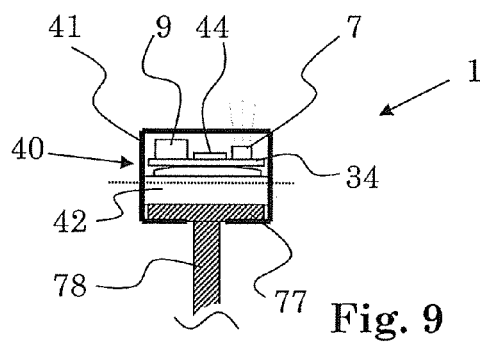
FIG. 9 a strongly schematized illustration of a tag attached at a plunger top by containing the plunger top.

FIG. 9 illustrates in a strongly schematized manner a tag 1 attached at a plunger top 77 by containing the plunger top 77. The tag can be a tag as described elsewhere herein, e.g., in FIG. 1 or 2. The housing 41, symbolized by thick lines, has an opening through or into which plunger rod 78 extends.

PCB 34 of tag 1 is present between battery 42 and the electronic components of tag 1.

In order to be able to insert electronics unit 40 into housing 41, the latter may be dividable into two (or possibly more) parts, e.g., along the dotted line in FIG. 9.

Plunger rod 78 may be fixed to plunger top 77, e.g., by a threading (not illustrated in FIG. 9).

However, plunger rod 78 may alternatively be integrally formed with plunger top 77, e.g., the two being a single injection molded part. In this case, for assembling housing 41 and the plunger top/plunge rod part, the lower half of housing 41 (which has the above-mentioned hole) may be pushed over the plunger rod, with the hole, from the free end of plunger rod 78. With the two housing halves still separate, electronics unit 40 can be inserted into housing 41, and then, housing 41 can be closed, which in addition attaches tag 1 to plunger top 77.

Figure 10:
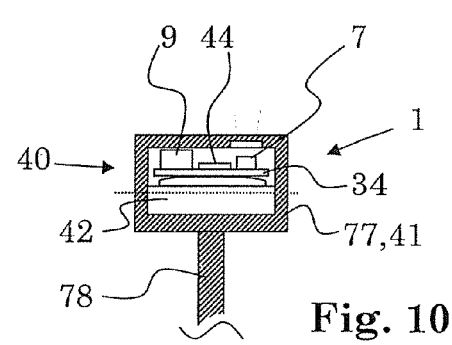
FIG. 10 a strongly schematized illustration of a plunger top with integrated tag.

FIG. 10 is a strongly schematized illustration of a plunger top 77 with integrated tag 1. In this case, plunger top 77 constitutes a housing 41 for at least a portion of tag 1, in particular for electronics unit 40. If a rip strip is comprised in a tag, the rip strip will usually not be housed by a housing 41. A part illustrated in FIG. 10 fulfills the functions of both, being the plunger top for or of a syringe, and being a housing for at least a portion of an electronic tag.

The housing 41 of FIG. 10 may be dividable into two (or possibly more) parts, e.g., along the dotted line in FIG. 10.

The housing in FIG. 9 and also the housing 41 in FIG. 10 may be integrally formed, e.g., being a single molded part.

Figure 11:
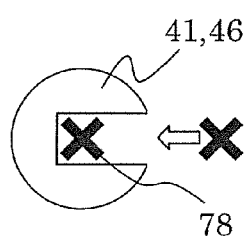
FIG. 11 a strongly schematized illustration of an assembly step inserting a plunger rod into a housing portion of a tag.

FIG. 11 is a strongly schematized illustration of an assembly step inserting a plunger rod 78 into a housing portion 46 of a tag 1. FIG. 11 can be seen in conjunction with FIG. 9, since in both cases, a plunger rod 78 may have to be inserted into an opening of a housing part (referenced 46 in FIG. 11), so as to provide that a plunger top 77 is present inside a housing 41 of a tag 1, whereas a plunger rod 78 extends out of the housing 41. With the opening being designed as sketched in FIG. 11, plunger rod 78 can be entered sideways. This can be useful in particular if a plunger seal is present at an end of the plunger rod 78 which cannot be removed, e.g., the plunger assembly already being assembled with the barrel of the syringe.

Figure 12:
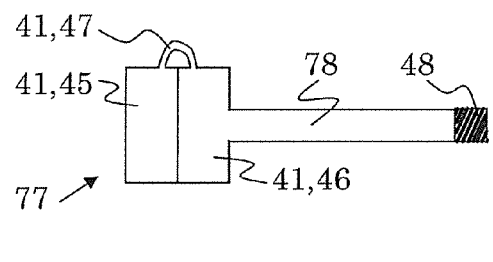
FIG. 12 a strongly schematized illustration of a constituent of a plunger assembly including plunger top and plunger rod and integrating a foldable housing for an electronic tag.
Figure 13:
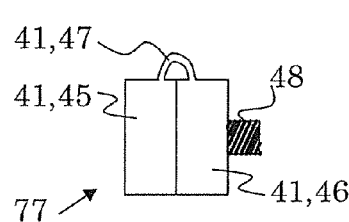
FIG. 13 a strongly schematized illustration of a plunger top integrating a foldable housing for an electronic tag.
Figure 14:
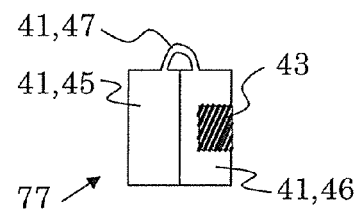
FIG. 14 a strongly schematized illustration of a plunger top integrating a foldable housing for an electronic tag.

FIGS. 12 to 14 can be seen in conjunction with FIG. 10, since they concern the configuration in which a part of the tag is integrated in a part of the plunger assembly, more particularly in the plunger top 77. In FIGS. 12 to 14, the housing 41 includes a first housing portion 45 and a second housing portion 46 which are interconnected by a folding portion 47. All these parts may be integrally formed. They may, e.g., be a single injection molded part.

FIG. 12 is a strongly schematized illustration of a constituent of a plunger assembly including plunger top 77 and plunger rod 78 and integrating a foldable housing 41 for an electronic tag 1. In this case, housing 41, plunger top 77 and plunger top 78 are integrally formed. Plunger rod 78 may have, as illustrated in FIG. 12, an outer threading 48 for connecting it to a plunger seal. Other ways of establishing the connection may be provided, e.g., bonding, and a plunger seal may also be integrated.

FIG. 13 is a strongly schematized illustration of a plunger top 77 integrating a foldable housing 41 for an electronic tag 1. In this case, plunger top 77 includes an outer threading 48 for attaching a plunger rod. Also here, other ways of establishing the desired connection may be applied, e.g., bonding.

FIG. 14 is a strongly schematized illustration of a plunger top 77 integrating a foldable housing 41 for an electronic tag 1, wherein in this case, plunger top 77 includes an inner threading 43 for attaching a plunger rod. Also here, other ways of establishing the desired connection may be applied, e.g., bonding.

Figure 15:
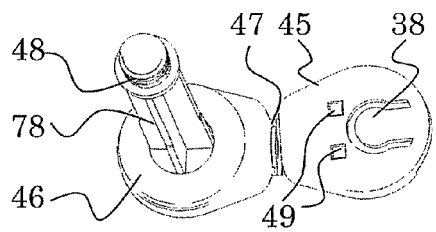
FIG. 15 a perspective view onto an assembly including a plunger top/plunger rod part and a housing of an electronic tag.

FIG. 15 is a perspective view onto an assembly of a plunger top 77/plunger rod 78 part (which in particular may be integrally formed, cf. also the description concerning FIGS. 9 and 11) and a housing 41 of an electronic tag 1. Plunger rod 78 is pushed through the opening in a second portion 46 of housing 41. The second portion 46 is foldable onto a first portion 45 of housing 41. The two housing portions are interconnected by a folding portion 47 of housing 41, which may be resilient due to its (reduced) thickness, or the material of which housing 41 is made is (generally) sufficiently resilient.

Figure 16:
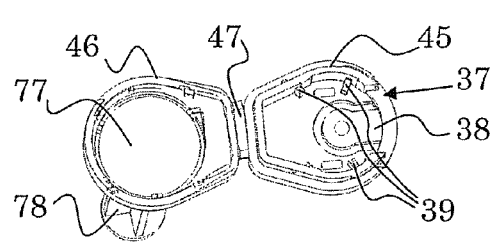
FIG. 16 a different perspective view onto the assembly of FIG. 15.

First housing portion 45 provides two transparent portions which may be windows (in particular be having a reduced thickness) or openings (not drawn in FIG. 16). LEDs of a display unit of an electronics unit to be inserted into housing 41 are better visible this way.

In addition, housing 41 provides a flexible portion 38 which is defined by a slit in housing 41. A switch of an electronics unit to be inserted into housing 41 can be more easily approached this way. Pushing the flexible portion 38 from outside housing 41 can allow to readily operate a switch positioned below the flexible portion 38.

The two housing portions 45, 46 can be designed to establish a snap fit. This way, housing 41 can be readily closed (after inserting the electronics unit), and a well-defined alignment of the housing parts can be achieved this way.

FIG. 16 is a different perspective view onto the assembly of FIG. 14. In this view, the inside of housing 41 can be seen. Plunger top 77 is present inside housing 41.

Housing 41 includes another opening, referenced 37, through which a rip strip (if present in the tag) may extend out of housing 41.

Furthermore, housing 41 provides a holder or fixture for a constituent of the tag, in particular for a battery of the tag. For establishing this, e.g., protrusions 39 like illustrated in FIG. 16, e.g., ribs, may be provided.

Figure 17:
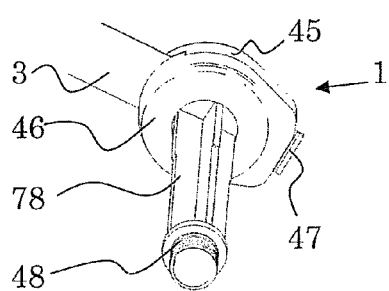
FIG. 17 a perspective view onto an assembly including a plunger top/plunger rod part and an electronic tag.

FIG. 17 is a perspective view onto an assembly of a plunger top 77/plunger rod 78 part and an electronic tag 1. FIG. 17 may be understood as the assembly of FIGS. 15 and 16, but including the tag 1. Housing 41 is closed, portions 45 and 46 are snapped into each other, and the electronics unit 40 is inserted. A rip strip 3 of tag is extends out of housing 41.

Figure 18:
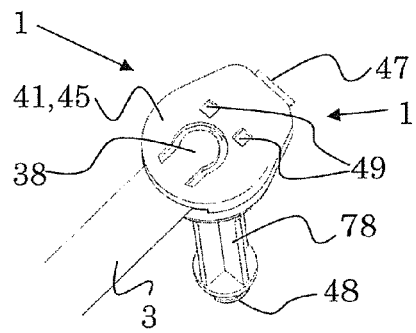
FIG. 18 a perspective view onto an assembly of a plunger top/plunger rod part and an electronic tag.

FIG. 18 is a perspective view onto an assembly of a plunger top 77/plunger rod 78 part and an electronic tag 1.

A first way of interpreting FIG. 18 is to understand it as another view of the assembly of FIG. 17.

However, the assembly of FIG. 18 can also be understood, in a second interpretation, as illustrating an example for an integrated tag. In this case, housing 41 establishes plunger top 77 or, vice versa, plunger top 77 establishes housing 41 of the tag 1. Thus, a single integrally formed part may include housing 41 (including all its parts) and plunger top 77 and, optionally also plunger rod 78. FIGS. 12 to 14 schematically various possible variations.

Figure 19:
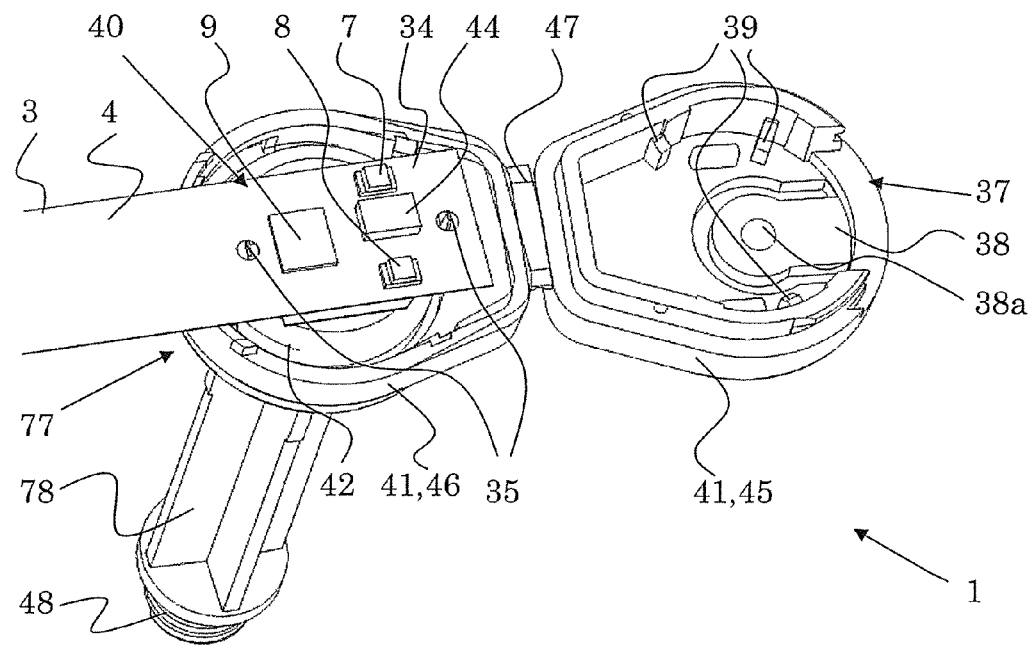
FIG. 19 a perspective view onto the assembly of FIG. 18, but with open housing.

FIG. 19 is a perspective view onto an assembly of FIG. 18, but with housing 41 open. It may be interpreted in the same two ways as FIG. 18 can be interpreted.

Electronics unit 40 and its constituents are well visible in FIG. 19. Battery 42 is connected to PCB 34 via two contacts 35. Battery contact leads may be bonded to battery 42 which lead to the contacts 35.

At flexible portion 38, a protrusion 38a may be provided which facilitates operating switch 9 (with housing 41 closed).

Figure 20:
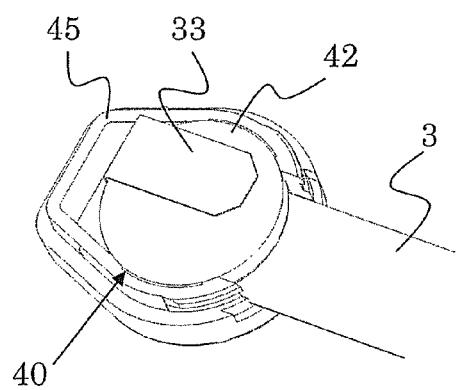
FIG. 20 a perspective view onto a portion of the assembly of FIGS. 18 and 19.

FIG. 20 is a perspective view onto a portion of the assembly of FIGS. 18 and 19. In FIG. 20, housing portion 46 is not drawn, but housing portion 45 is. The electronics unit 40 is inserted in housing portion 45. Since, in the embodiments of FIGS. 16, 19 and 20, battery clamping takes place in housing portion 45, insertion of electronics unit 40 is accomplished rather in the way suggested by in FIG. 20 than in FIGS. 16 and 19.

A battery contact lead 33 contacting battery 42 is visible in FIG. 20.

Described arrangements of the tag and the switch at the plunger top allow to make sure that a person about to use (operate) the syringe will, practically inevitably, effect a display of the integrity status. Pressing against the plunger top or a portion of the tag present there for pressing some of the pharmaceutical product or air present in the syringe out of the syringe can result in operating the switch ("display switch"), such that the integrity status is displayed. In case the display indicates that the pharmaceutical product has been exposed to detrimental conditions, an injection of (probably) perished medication can be avoided.

The tag, the package and the packaged pharmaceutical product described in the present patent application are easy to use and operable by untrained personnel, i.e. by people not specifically instructed on how to use the tag, the package, the packaged pharmaceutical product, as far as the integrity monitoring is concerned. Patients and health care specialists who apply or use the pharmaceutical product can, without additional measures and without the need of additional tools, check the integrity of the product to be applied or used. And this can be accomplished (at least approximately) at the time when the product is applied or used. Suitably positioning the tag and in particular the (display) switch can make a display of status data (practically) unavoidable at the time the syringe (and the pharmaceutical product) is about to be used, cf. above.

It can happen that pharmaceutical products are returned from the acquirer or user (e.g., patient or health care specialist) to the manufacturer or the distributor without having been used. This sometimes is the case, e.g., in case of particularly valuable products.

If the product is returned to the manufacturer or distributor, the manufacturer or distributor can check the integrity status of the product by using the tag. Based thereon, it can, e.g., be decided whether or not to forward the product to another acquirer or user.

Independently of having checked the integrity status or not, it may be provided that the manufacturer or distributor forwards the product to another acquirer or user. That other acquirer or user can then (e.g., when the product is about to be applied) check the integrity status of the product using the herein described tag and the package, respectively.

It shall be noted that the tag, the package and the packaged pharmaceutical product provide standalone solutions which do not require further equipment, at least not for having the integrity status of the product displayed. And the attaching of the tag to the syringe can be accomplished by the manufacturer or by the packaging company packaging the product in a box.

The tag may consist of merely:
an electronics unit; and
a PCB (typically a flexible PCB) forming, if present, the rip strip, and the PCB on which the components of the electronics unit are mounted;
wherein the electronics unit may consist merely of:
a switch (and possibly also a second switch—namely, e.g., for starting the monitoring);
one or more, typically two, light emitters, typically LEDs;
an integrated circuit (embodying at least the control unit); and
an energy source such as a battery;
wherein, if the one or more sensors are not integrated in the integrated circuit, at least one sensor is, in addition, comprised, too, in the electronics unit, and
wherein optionally up to four capacitors and/or up to four resistors may be comprised, too, in the electronics unit. And typically, all components comprised in the electronics unit are mounted on the PCB, more precisely on one and the same PCB.

Note that the PCB can be sufficient for electrically contacting the energy source (battery), cf. FIGS. 2, 3, such that no separate battery holder or battery holder leads needs to be provided. However, the battery may be contacted by one or more (typically two) contact leads—which again are operationally (and usually galvanically) connected to the PCB, cf. FIGS. 19, 20.

And note furthermore, that it is possible that the rip strip is dispensed with (at least in its function as providing a means for starting the monitoring) and/or the switch may be dispensed with (at least in its function as a means for requesting a displaying of the status data, and this at least for times not coinciding with the time of terminating the monitoring).

A display of an above-described kind can be particularly small and cost-efficient. There is no need for a liquid crystal display or the like.

The invention claimed is:

1. A package for a pharmaceutical product, said package comprising
a syringe;
an electronic tag for obtaining information relating to the integrity of the product as assessed from an exposure of said product to physical or environmental conditions during a time span;
wherein
I) said tag is attached at or to a constituent of said syringe; or
II) at least a portion of said tag is integrated in a constituent of said syringe;
and wherein said tag comprises an electronics unit comprising
a control unit;
a sensor unit comprising at least one sensor for monitoring said physical or environmental conditions;
a display unit comprising a display for displaying data relating to said integrity referred to as status data;
a switch;
wherein said control unit is structured and configured for effecting that said display unit displays said status data in reaction to an operation of said switch.

2. The package according to claim 1, wherein said constituent of said syringe is a plunger top.

3. The package according to claim 1, wherein a housing of said tag is integrated in said constituent of said syringe.

4. The package according to claim 1, wherein the tag is attached to or at said constituent of the syringe, and wherein at least a portion of said constituent of the syringe is contained in the tag or in a constituent of the tag, more specifically in a housing of the tag.

5. The package according to claim 3, wherein and said housing and said constituent of said syringe are integrally formed.

6. The package according to claim 4, wherein said constituent of said syringe is a plunger top, the syringe comprising a plunger rod, wherein a constituent of the tag has an opening, said plunger rod extending into or through said opening.

7. The package according to claim 1, wherein the package comprises a pressing surface for operating said syringe by pressing against said pressing surface, and wherein said pressing surface is provided by said tag, and wherein said switch is structured and arranged in such a way that it is operated when pressure is exerted against said pressing surface for operating the syringe.

8. The package according to claim 1, wherein the tag comprises a housing comprising a first and a second housing portion which are mutually attachable by establishing a snap fit with one another.

9. The package according to claim 1, wherein the tag comprises a rip strip comprising a breakable electrical connection operationally connected to said control unit.

10. The package according to claim 1, wherein said display unit comprises one or more light emitters for emitting light pulses, and wherein said status data is encoded in a sequence of light pulses emitted by said one or more light emitters.

11. A packaged pharmaceutical product, comprising a package according to claim 1 and said pharmaceutical product, wherein said pharmaceutical product is contained in said syringe.

12. A device, comprising
a plunger top for use in or with a syringe for applying a pharmaceutical product; and
an electronic tag for obtaining information relating to the integrity of a product as assessed from an exposure of said product to physical or environmental conditions during a time span;
wherein
I) said tag is attached at or to said plunger top; or
II) at least a portion of said tag is integrated in said plunger top; and wherein said tag comprises an electronics unit comprising
a control unit;
a sensor unit comprising at least one sensor for monitoring said physical or environmental conditions;
a display unit comprising a display for displaying data relating to said integrity referred to as status data;
a switch;
wherein said control unit is structured and configured for effecting that said display unit displays said status data in reaction to an operation of said switch.

13. A device, comprising a plunger top for use in or with a syringe for applying a pharmaceutical product, wherein said plunger top establishes a housing suitable for receiving at least a portion of an electronic tag for obtaining information relating to the integrity of a product as assessed from an exposure of said product to physical or environmental conditions during a time span;

and wherein said tag comprises an electronics unit comprising a control unit;

a sensor unit comprising at least one sensor for monitoring said physical or environmental conditions;

a display unit comprising a display for displaying data relating to said integrity referred to as status data;

a switch;

wherein said control unit is structured and configured for effecting that said display unit displays said status data in reaction to an operation of said switch.

14. A method for manufacturing a package for a pharmaceutical product, the method comprising the steps of A) providing at least one constituent of a syringe for applying said pharmaceutical product;

B) providing an electronic tag for obtaining information relating to the integrity of said product as assessed from an exposure of said product to physical or environmental conditions during a time span;

the method further comprising the step of

CI) attaching said tag to said at least one constituent of said syringe;

or the step of

CII) integrating at least a portion of said tag in a constituent of said syringe;

and wherein said tag comprises an electronics unit comprising a control unit;

a sensor unit comprising at least one sensor for monitoring said physical or environmental conditions;

a display unit comprising a display for displaying data relating to said integrity referred to as status data;

a switch;

wherein said control unit is structured and configured for effecting that said display unit displays said status data in reaction to an operation of said switch.

15. A method according to claim 14, comprising the step of manufacturing a unitary or an integrally formed part which establishes said constituent of the syringe and an openable housing for at least a part of the tag.

16. A method for monitoring an integrity of a pharmaceutical product, the method comprising the steps of a) providing a syringe;

b) providing

I) an electronic tag attached at or to a constituent of said syringe; or

II) an electronic tag at least a portion of which is integrated in a constituent of said syringe;

said syringe comprising a barrel, said barrel containing said pharmaceutical product; said tag being a tag for obtaining information relating to the integrity of said product as assessed from an exposure of said product to physical or environmental conditions during a time span, the tag comprising an electronics unit comprising a control unit;

a sensor unit comprising at least one sensor for monitoring said physical or environmental conditions;

a display unit comprising a display for displaying data relating to said integrity referred to as status data;

a switch;

wherein said control unit is structured and configured for effecting that said display unit displays said status data in reaction to an operation of said switch.

17. The package according to claim 9, wherein a breaking of said breakable electrical connection indicates the end of said time span or the beginning of said time span.

18. The package according to claim 1, wherein said data is encoded in one or more of the color of the light pulses;

a duration of the light pulses;

the number of the light pulses in the sequence.

* * * * *